United States Patent [19]

Uenishi et al.

[11] Patent Number: 5,565,300

[45] Date of Patent: * Oct. 15, 1996

[54] POSITIVE PHOTORESIST COMPOSITION

[75] Inventors: Kazuya Uenishi; Shinji Sakaguchi; Tadayoshi Kokubo, all of Shizuoka, Japan

[73] Assignee: Fuji Photo Film Co., Ltd., Kanagawa, Japan

[ * ] Notice: The portion of the term of this patent subsequent to Apr. 26, 2010, has been disclaimed.

[21] Appl. No.: 647,904

[22] Filed: Jan. 30, 1991

[30] Foreign Application Priority Data

Feb. 1, 1990 [JP] Japan ................................. 2-022679

[51] Int. Cl.$^6$ .................................................. G03F 7/023
[52] U.S. Cl. ........................... 430/192; 430/165; 430/191; 430/193
[58] Field of Search ................................ 430/192, 193, 430/165, 166, 191

[56] References Cited

U.S. PATENT DOCUMENTS

| | | | |
|---|---|---|---|
| 4,499,171 | 2/1985 | Hosaka et al. | 430/192 |
| 4,587,196 | 5/1986 | Toukhy | 430/192 |
| 4,626,492 | 12/1986 | Eilbeck | 430/192 |
| 4,628,020 | 12/1986 | Stahlhofen | 430/165 |
| 4,859,563 | 8/1989 | Miura et al. | 430/192 |
| 4,863,828 | 9/1989 | Kawabe et al. | 430/192 |
| 4,883,739 | 11/1989 | Sakaguchi et al. | 430/192 |
| 5,001,040 | 3/1991 | Blakeney et al. | 430/192 |
| 5,019,478 | 5/1991 | Toukhy et al. | 430/165 |
| 5,059,507 | 10/1991 | Uetani et al. | 430/192 |
| 5,087,548 | 2/1992 | Hosaka et al. | 430/193 |
| 5,089,373 | 2/1992 | Uenishi et al. | 430/192 |
| 5,153,096 | 10/1992 | Uenishi et al. | 430/193 |
| 5,215,857 | 6/1993 | Hosaka et al. | 430/192 |

FOREIGN PATENT DOCUMENTS 363978 4/1990 European Pat. Off. .
395049 10/1990 European Pat. Off. .

OTHER PUBLICATIONS

Patent Abstracts of Japan, vol. 12, No. 253 (P–731)(3100) Jul. 16, 1988, & JP–A–63 043134 (Mitsubishi Chem Ind Ltd) Feb. 24, 1988.

*Primary Examiner*—John S. Y. Chu
*Attorney, Agent, or Firm*—Sughrue, Mion, Zinn, Macpeak & Seas

[57] ABSTRACT

A photoresist composition is disclosed containing an alkali-soluble resin and a photosensitive substance obtained by reaction of a polyhydroxy compound and (a) a 1,2-naphthoquinonediazido-5-(and/or -4-)sulfonyl chloride(s), said photosensitive substance being a mixture of photosensitive compounds (1) to (3):

(1) a photosensitive compound having at least one hydroxyl group per molecule and having a number ratio of 1,2-naphthoquinonediazido-5-(and/or -4-)sulfonyl chloride sulfonate groups to hydroxyl groups within the range of from 3 to 20, contained in the photosensitive substance in an amount of 50 wt % or more;

(2) a photosensitive compound where all the hydroxyl groups in the polyhydroxy compound have been 1,2-naphthoquinonediazidosulfonyl-esterified, contained in the photosensitive substance in an amount of 30 wt % to 0 wt %; and (3) a photosensitive compound having three or more hydroxyl groups which have not been 1,2-naphthoquinonediazidosulfonyl-esterified per molecule, contained in the photosensitive substance in an amount of 20 wt % to 0 wt %.

The composition is suitable to exposure with g-ray, i-ray and excimer laser to provide a sharp resist image. The photoresist composition also has high sensitivity, high resolving power, precise reproducibility to provide resist images having good sectional shapes, broad development latitude, high heat resistance and good storage stability.

10 Claims, No Drawings

POSITIVE PHOTORESIST COMPOSITION

FIELD OF THE INVENTION

The present invention relates to a positive photoresist composition sensitive to radiation. More particularly, the present invention relates to a positive photoresist having high resolving power and sensitivity, and which is especially useful for forming fine patterns with good sectional shapes. The positive photoresist composition of the invention can be coated onto a substrate such as a semiconductor wafer, glass, ceramic or metal in a thickness of from 0.5 to 3 μm by, for example, spin coating or roller coating. Afterwards, the coated layer is heated and dried, and a circuit pattern or the like is printed on the layer, for example, by irradiation with ultraviolet rays through a mask. Then, the exposed photoresist layer is developed to form a positive image pattern on the substrate. Furthermore, the substrate can be etched using the positive image as a mask, to thereby form the intended pattern on the substrate. The positive photoresist of the present invention is applicable to, for example, manufacture of semiconductors such as IC or the like, manufacture of circuit plates for liquid crystal devices or thermal heads, and other photofabrication processes.

BACKGROUND OF THE INVENTION

A positive photoresist composition generally contains an alkali-soluble resin and a photosensitive substance of a naphthoquinonediazide compound. For example, novolak type phenol resins/naphthoquinonediazide substituent compounds are described in U.S. Pat. Nos. 3,666,473, 4,115,128 and 4,173,470; and examples of the most typical compositions include cresol-formaldehyde novolak resins/trihydroxybenzophenone-1,2-naphthoquinonediazidosulfonates as described in L. F. Thompson, *Introduction to Microlithography* (published by ACS Publishing Co., No. 219, pages 112 to 121).

Novolak resins used as a binder are soluble in an aqueous alkaline solution but do not swell therein and are highly resistant to plasma etching when the image pattern is used as an etching mask, such that novolak resins are especially advantageous. On the other hand, naphthoquinonediazide compounds when used alone as a photosensitive substance act as a dissolution inhibitor to lower the alkali solubility of a novolak resin, but are decomposed by light irradiation to release an alkali-soluble substance which elevates the alkali solubility of the novolak resin. Due to the light dependent variation of the properties of these compounds, naphthoquinonediazide compounds are especially useful as a photosensitive substance component in a positive photoresist composition.

Hitherto, various resists have been proposed in order to obtain a high resolving power needed for processing of ultrafine patterns. One such photoresist composition contains a complete ester as a photosensitive component, wherein all the hydroxyl groups of a polyhydroxy compound have been esterified by elevating the esterification degree.

JP-A-61-45240 (the term "JP-A" as used herein refers to a "published unexamined Japanese patent application") describes the use of 1,2-naphthoquinonediazidotrisulfonates of trihydroxybenzenes. JP-A-61-118744 and JP-A-62-280737 describes the use of 1,2-naphthoquinonediazidotetrasulfonates of tetrahydroxybenzophenones. Resists containing such 1,2-naphthoquinonediazidosulfonates having an elevated esterification degree as a photosensitive component have a high resolving power but exhibit low sensitivity, such that manufacturing efficiency is decreased. The sensitivity could be enhanced by reducing the proportion of the photosensitive component in the resist, or by addition of a sensitizing agent to the resist, or by elevating the alkali activity of the developer for processing the exposed resist. In such cases, however, the resolving power of the resist is substantially degraded such that the resist is no longer useful for forming ultrafine patterns.

Elevation of the esterification degree alone therefore does not provide both high resolving power and high sensitivity. "Elevation of esterification degree" as used herein means an increase in the proportion of the complete ester form of the light-sensitive component.

It is well known by those skilled in the art that a 1,2-naphthoquinonediazidosulfonate of a polyhydroxy compound which is conveniently used in a positive photoresist composition is not a single compound but a mixture of many isomers.

For example, U.S. Pat. Nos. 4,409,314 and 4,439,516 and JP-A-62-280737 describe that 1,2-naphthoquinonediazidosulfonates of dihydroxybenzophenone or trihydroxybenzophenone are in the form of a mixture of the esters.

U.S. Pat. No. 3,148,983 describes a 1,2-naphthoquinonediazidotrisulfonate of tetrahydroxybenzophenone, which description is not considered to be completely technically accurate. N. Ogata et al found that the ester is also in the form of a mixture of plural isomers thereof, as disclosed in *Functional Materials,* pages 43 to 46 (December, 1987).

The present inventors isolated and purified particular isomers other than the complete ester in various photosensitive substances and evaluated and investigated the resist capacity of the isomers. As a result, the present inventors have discovered certain isomers having extremely high sensitivity and high resolving power which could not be expected from conventional resists containing 1,2-naphthoquinonediazidosulfonates of polyhydroxy compounds in the form of various mixtures of the esters.

Furthermore, the present inventors have discovered a novel method of efficiently producing these isomers.

SUMMARY OF THE INVENTION

Some objects of the present invention are to provide (1) a positive photoresist composition having high resolving power and high sensitivity, (2) a positive photoresist composition which accurately reproduces the mask dimension over a broad range of photomask line width values, (3) a positive photoresist composition which provides a developed resist pattern having a line width of 1 μm or less and a cross-sectional shape having a high aspect ratio, (4) a positive photoresist composition which may form a developed resist pattern having such a nearly vertical side wall of a cross-section of the pattern, (5) a positive photoresist composition having a broad development latitude, and (6) a positive photoresist composition which forms a developed resist image having excellent heat resistance, which is especially useful in manufacture of semiconductor devices.

The present inventors have resolutely investigated various positive photoresist compositions in consideration of the above described problems of the prior art compositions and, as a result, have found that the objects of the present invention are attained by a positive photoresist composition containing an alkali-soluble resin and a photosensitive substance prepared by the reaction of a polyhydroxy compound and (a) 1,2-naphthoquinonediazido-5-(and/or -4-) sulfonyl chloride(s), said photosensitive substance being a mixture of photosensitive compounds (1) to (3):

(1) a photosensitive compound having at least one hydroxyl group per molecule and having a number ratio of 1,2-naphthoquinonediazido-5-(and/or -4-)sulfonyl chloride sulfonate groups to hydroxyl groups within the range of from 3 to 20, contained in the photosensitive substance in an amount of 50 wt % or more;

(2) a photosensitive compound where all the hydroxyl groups in the polyhydroxy compound have been 1,2-naphthoquinonediazidosulfonyl-esterified, contained in the photosensitive substance in an amount of 30 wt % or less; and (3) a photosensitive compound having three or more hydroxyl groups which have not been 1,2-naphthoquinonediazidosulfonyl-esterified per molecule, contained in the photosensitive substance in an amount of 20 wt % or less.

DETAILED DESCRIPTION OF THE INVENTION

The present invention is explained in detail below.

The photosensitive substance for use in the present invention is a mixture of the following compounds (1) to (3) as represented by the formula (I) and which mixture is obtained by the reaction of a polyhydroxy compound and (a) 1,2-naphthoquinonediazido-5-(and/or -4-)sulfonyl chloride(s).

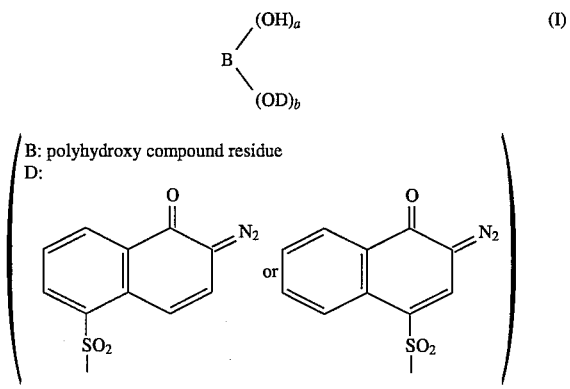

(1) $1 \leq a \leq 2$, and $b/a = 3/1$ to $20/1$ (number ratio), contained in the photosensitive substance in an amount of 50 wt % or more;

(2) $a=0$, and $1 \leq b$ (complete ester), contained in the photosensitive substance in an amount of 30 wt % to 0 wt %; and (3) $3 \leq a$, and $0 \leq b$, contained in the photosensitive material in an amount of 20 wt % to 0 wt %.

Particularly, the polyhydroxy compound may be reacted with a 1,2-naphthoquinonediazido-4-sulfonyl chloride, or both the -5- and -4-sulfonyl chlorides.

In the component (1), the case where $a=1$ is preferred. The ratio $b/a$ is from 3/1 to 20/1, preferably from 4/1 to 12/1, more preferably from 5/1 to 9/1. If the ratio $b/a$ is less than 3/1, the film retention percentage is noticeably lower. However, if the ratio $b/a$ is more than 20/1, the sensitivity rapidly diminishes.

The content of the component (1) of the photosensitive substance is 50 wt % or more, preferably 60 wt % or more, more preferably 70 wt % or more. If it is less than 50 wt %, the resolving power is lowered.

The content of the component (2) of the complete ester of the photosensitive substance is preferably 30 wt % to 0 wt %. If it is more than 30 wt %, the sensitivity is lowered. More preferably, the content of component (2) is 20 wt % to 0 wt %, especially preferably 15 wt % to 0 wt %.

The content of the component (3) containing three or more OH groups per molecule of the photosensitive substance is 20 wt % to 0 wt %. If more than 20 wt %, the resist profile is noticeably deteriorated and the resolving power is also noticeably lowered. More preferably, the content of component (3) is 15 wt % to 0 wt %, especially preferably 10 wt % to 0 wt %.

The present inventors have developed the following three methods for preparing the photosensitive substance of the present invention.

1) A part where $b/a=3/1$ to $20/1$ (as a number ratio) of formula (I) is isolated by column chromatography from a mixture of various isomers obtained by the general reaction of a polyhydroxy compound and a 1,2-naphthoquinonediazidosulfonyl chloride.

2) A selective reaction is carried out between a polyhydroxy compound and a 1,2-naphthoquinonediazidosulfonyl chloride, where selectivity is imparted to the hydroxyl groups of the polyhydroxy compound by an electronic or steric effect. The resulting compound is reacted with the chloride in a mixed solvent comprising an organic solvent and water to provide selective esterification.

3) A predetermined number of the hydroxyl groups in a polyhydroxy compound are protected, and thereafter any remaining free hydroxyl groups in the compound are esterified with a 1,2-naphthoquinonediazidosulfonyl chloride. After esterification, the protective groups are removed to recover free hydroxyl groups.

The method 1) is useful on a laboratory scale, but the methods 2) and 3) are more suitable than 1) as an industrial process. However, the method 3) is disadvantageous with respect to the stability of the 1,2-naphthoquinonediazido group upon removing the protective groups. Thus, the method 2) is best.

In the method 2), a particular skeleton compound (i.e., polyhydroxy compound) having an electronic or steric effect is reacted for esterification in a mixed solvent comprising an organic solvent and water, whereupon the reaction selectivity of the hydroxyl groups in the compound is greatly increased. The novel method 2) is an effective means for obtaining the photosensitive substance of the present invention.

The photosensitive compound is obtained by reaction of a polyhydroxy compound (which polyhydroxy compound has been treated to have an electronic effect such that the reaction of the hydroxyl groups with a 1,2-naphthoquinonediazidosulfonyl chloride is highly selective), and (a) 1,2-naphthoquinonediazidosulfonyl chloride(s) in a mixed solvent comprising an organic solvent and water. Particularly, the photosensitive substance is obtained by reacting a polyhydroxy compound having both at least one group represented by formula (II) and at least one group represented by formula (III) in the same molecule and (a) 1,2-naphthoquinonediazido-5-(and/or -4-) sulfonyl chloride(s) in a mixed solvent comprising an organic solvent and water. Preferred examples of the compounds constituting the photosensitive substance of the present invention are represented by formulae (VII) and (VIII).

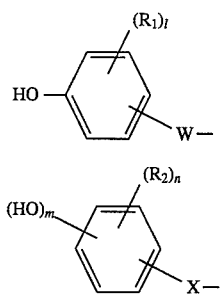  (II)

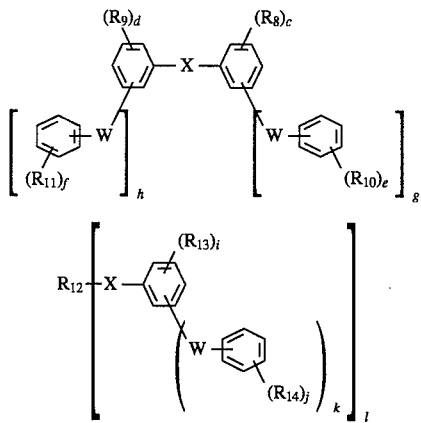 (III)

In the above formulae, W represents a linear or branched $C_1$ to $C_6$ alkylene group; X represents a divalent electron attracting group, preferably

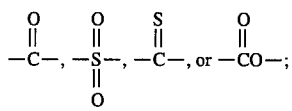

$R_1$ represents —H, a $C_1$ to $C_4$ alkyl group; $R_2$ represents —H, a $C_1$ to $C_4$ alkyl group, a halogen, a nitro group or a cyano group; l represents 0 or an integer of from 1 to 3; m represents an integer of from 1 to 4; and n represents or an integer of from 1 to 4.

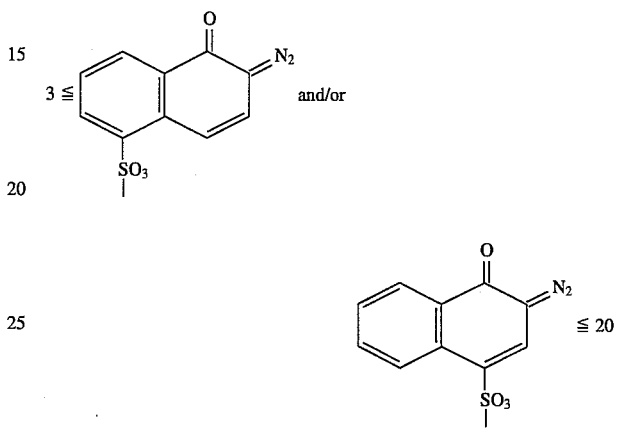 (VII)

(VIII)

In the above formulae, W represents a linear or branched $C_1$ to $C_6$ alkylene group; X represents a divalent electron attracting group, preferably

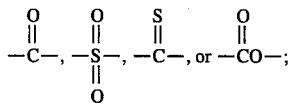

$R_{12}$ represents a $C_1$ to $C_4$ alkane residue, or a $C_6$ to $C_{12}$ aromatic residue; $R_8$ to $R_{11}$ and $R_{13}$ and $R_{14}$ may be the same or different and each represents —H, —OH, a substituted or unsubstituted $C_1$ to $C_8$ alkyl group, a substituted or unsubstituted $C_1$ to $C_8$ alkoxy group, a substituted or unsubstituted $C_6$ to $C_{15}$ aryl group, a substituted or unsubstituted $C_6$ to $C_{15}$ aralkyl group, a substituted or unsubstituted $C_2$ to $C_{15}$ acyl group, a substituted or unsubstituted $C_2$ to $C_{15}$ acyloxy group,

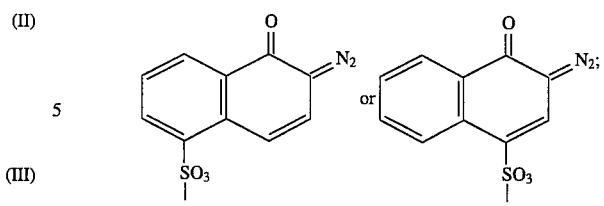

provided that one molecule of the photosensitive substance satisfies the following conditions:

$3 \leq$ 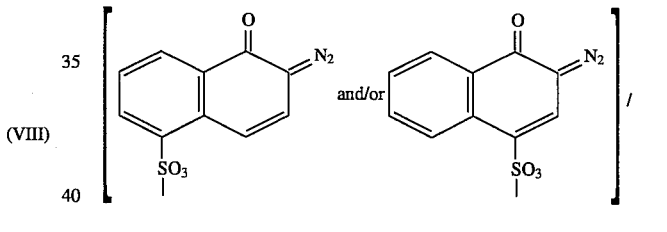 and/or

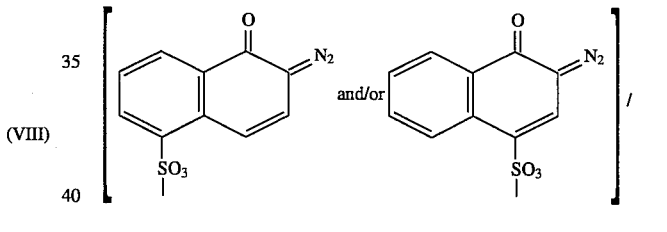 $\leq 20$ and the ratio of the number of groups $$\frac{\left[ \text{naphthoquinonediazidosulfonyl groups} \right]}{[-OH]}$$

is from 3/1 to 20/1; and c to l are average real numbers which satisfy the following conditions:

c–l:  $3 \leq (c + d) \leq 8$
$1 \leq (e + f) \leq 8$
$1 \leq (g + h) \leq 4$
$1 \leq i$–$l \leq 4$ The photosensitive compound can also be prepared by reaction of a polyhydroxy compound (which polyhydroxy compound has been treated to have a steric effect for selective reaction of the hydroxyl groups of the polyhydroxy compound with a 1,2-naphthoquinonediazidosulfonyl chloride), and a 1,2-naphthoquinonediazidosulfonyl chloride in a mixed solvent comprising an organic solvent and water. Preferably, the photosensitive compound is obtained by reacting a polyhydroxy compound having at least one group represented by formula (IV), (V) or (VI) per molecule and (a) 1,2-naphthoquinonediazido-5-(and/or -4-) sulfonyl chloride(s) in a mixed solvent comprising an organic solvent and water. Preferred examples of such compounds constituting the photosensitive substance of the present invention include those represented by formulae (IX) to (XVIII).

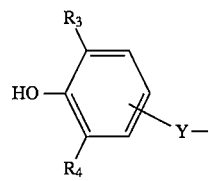
(IV)

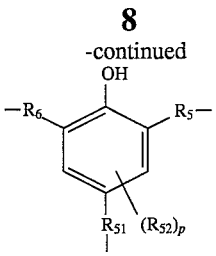
(VI)

where $R_3$ and $R_4$ each represents a linear or branched $C_1$ to $C_4$ alkyl or alkoxy group; and Y represents a divalent organic group, preferably a linear or branched $C_1$ to $C_4$ alkylene group,

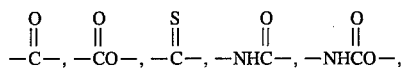

—S— or —O—, more preferably a linear or branched $C_1$ to $C_4$ alkylene group,

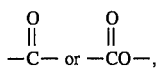

and especially preferably a linear or branched $C_1$ to $C_4$ alkylene group;

where $R_5$, $R_6$ and $R_{51}$ each represents a linear or branched $C_1$ to $C_4$ alkylene group; $R_7$ and $R_{52}$ may be the same or different and each represents —H, a substituted or unsubstituted $C_1$ to $C_8$ alkyl group, a substituted or unsubstituted $C_1$ to $C_8$ alkoxy group, a substituted or unsubstituted $C_6$ to $C_{15}$ aryl group, a substituted or unsubstituted $C_6$ to $C_{15}$ aralkyl group, a substituted or unsubstituted $C_2$ to $C_{15}$ acyl group, or a substituted or unsubstituted $C_2$ to $C_{15}$ acyloxy group; o represents an integer of from 1 to 3; and p represents 1 or 2.

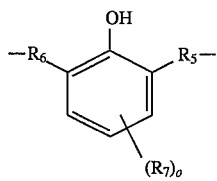
(V)

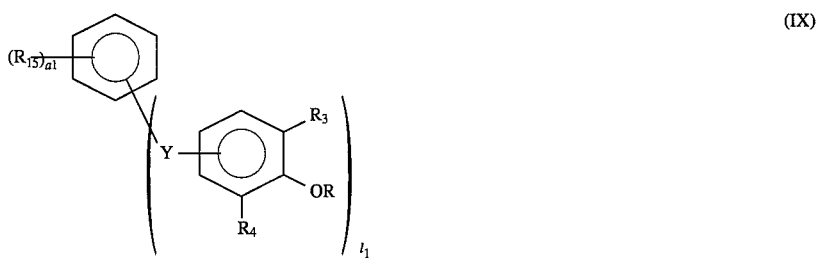
(IX)

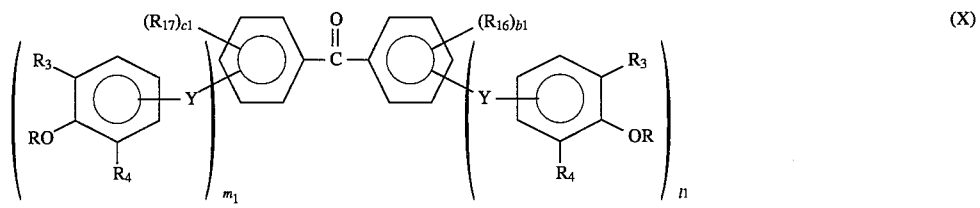
(X)

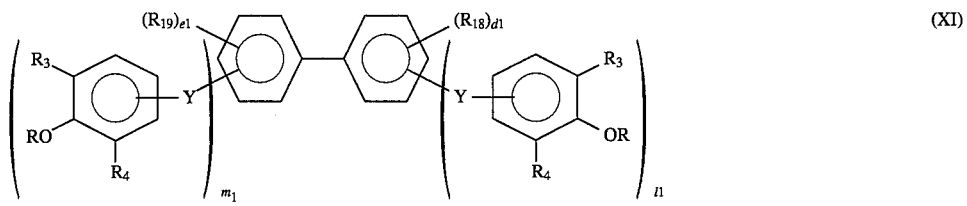
(XI)

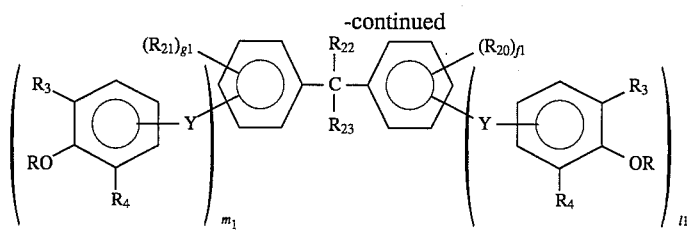
(XII)
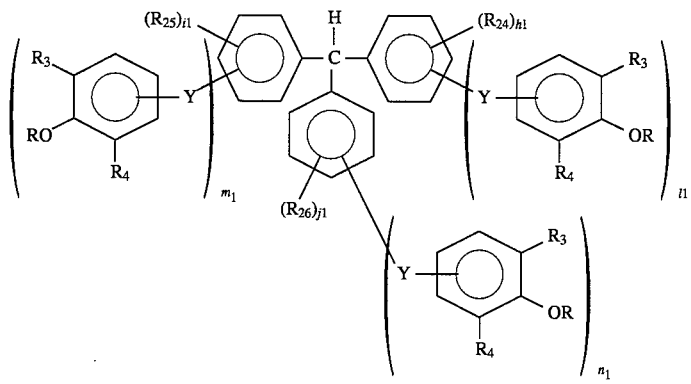
(XIII)
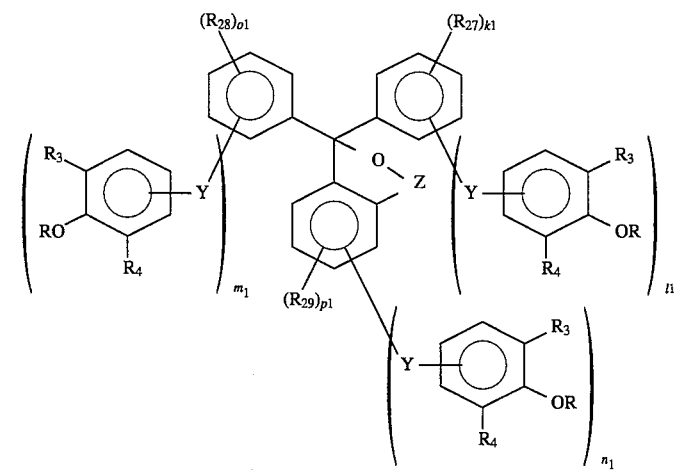
(XIV)
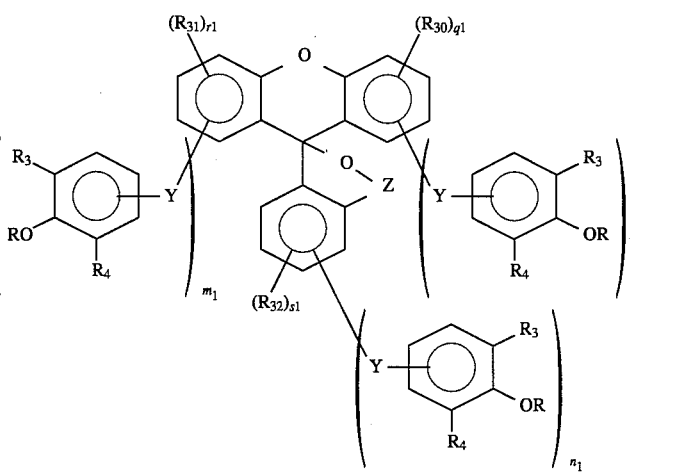
(XV)

-continued

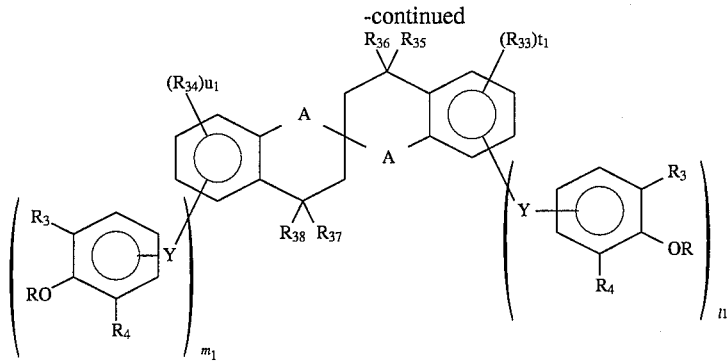
(XVI)

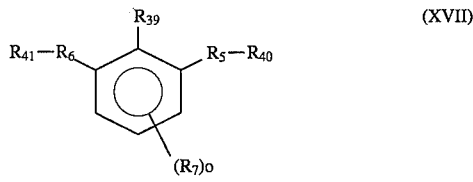
(XVII)

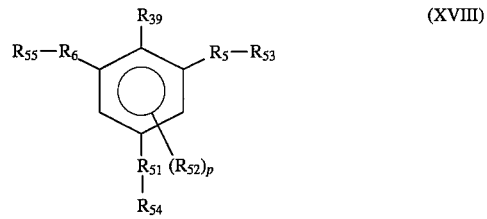
(XVIII)

In the above formulae, $R_3$ and $R_4$ each represents a linear or branched $C_1$ to $C_4$ alkyl or alkoxy group; Y represents a divalent organic group, preferably a linear or branched $C_1$ to $C_4$ alkylene group,

—S— or —O—, more preferably a linear or branched $C_1$ to $C_4$ alkylene group,

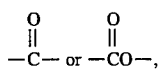

and especially preferably a linear or branched $C_1$ to $C_4$ alkylene group; R, which may be the same or different within the same molecule, represents —H,

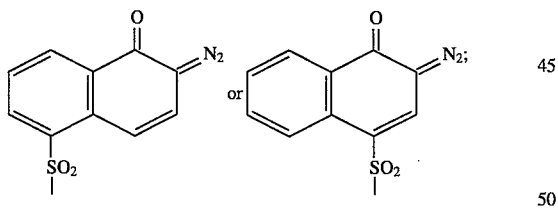

$R_{15}$ to $R_{21}$ and $R_{24}$ to $R_{34}$ may be the same or different and each represents —H, —OH, a substituted or unsubstituted $C_1$ to $C_8$ alkyl group, a substituted or unsubstituted $C_1$ to $C_8$ alkoxy group, a substituted or unsubstituted $C_6$ to $C_{15}$ aryl group, a substituted or unsubstituted $C_6$ to $C_{15}$ aralkyl group, a substituted or unsubstituted $C_2$ to $C_{15}$ acyl group, a substituted or unsubstituted $C_2$ to $C_{15}$ acyloxy group, or

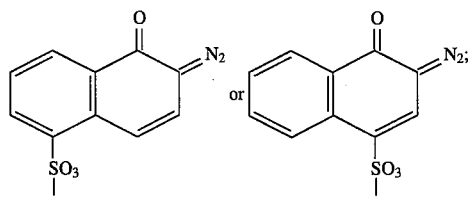

provided that one molecule of the photosensitive substance satisfies the following conditions:

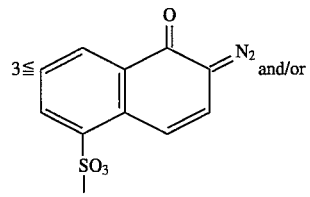

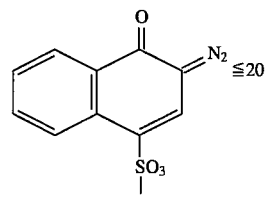

and the ratio of the number of groups

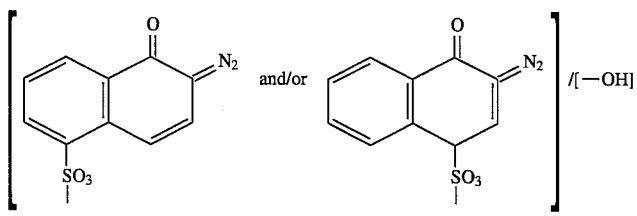

is from 3/1 to 20/1; and $R_{22}$ and $R_{23}$ each represents —H, —OH, —COOH, —CN, a halogen atom (e.g., F, Cl, Br), —COOR$_{43}$, —R$_{44}$—COOH, —R$_{45}$—COOR$_{46}$ (where $R_{43}$ and $R_{46}$ each represents a substituted or unsubstituted $C_1$ to $C_8$ alkyl group, a substituted or unsubstituted $C_6$ to $C_{15}$ aryl group, or a substituted or unsubstituted $C_6$ to $C_{15}$ aralkyl group; and $R_{44}$ and $R_{45}$ each represents a substituted or unsubstituted $C_1$ to $C_8$ alkylene group, or a substituted or unsubstituted $C_6$ to $C_{15}$ arylene group), or a substituted or unsubstituted $C_1$ to $C_8$ alkyl group, a substituted or unsubstituted $C_1$ to $C_8$ alkoxy group, or a substituted or unsubstituted $C_6$ to $C_{15}$ aralkyl group; Z represents —CO— or —SO$_2$—; A represents an oxygen atom or a single bond; a1 to u1 are average real numbers which satisfy the following conditions:

$$a1-u1: \quad 1 \leq a1 \leq 3$$
$$1 \leq l1 \leq 2$$
$$0 \leq m1, n1 \leq 2$$

$$3 \leq \begin{pmatrix} (b1+c1) \\ (d1+e1) \\ (f1+g1) \\ (t1+u1) \end{pmatrix} \leq 7$$

$$3 \leq \begin{pmatrix} (h1+i1+j1) \\ (k1+o1+p1) \\ (q1+r1+s1) \end{pmatrix} \leq 10$$

$R_{39}$ represents —OH; $R_5$, $R_6$ and $R_{51}$ each represents a linear or branched $C_1$ to $C_4$ alkylene group; $R_{35}$ to $R_{38}$ may be the same or different and each represents —H, —OH, a substituted or unsubstituted $C_1$ to $C_8$ alkyl group, a substituted or unsubstituted $C_1$ to $C_8$ alkoxy group, or a substituted or unsubstituted $C_6$ to $C_{15}$ aralkyl group; and $R_{40}$, $R_{41}$, $R_{53}$, $R_{54}$ and $R_{55}$ each represents a residue of any one of formulae (IX) to (XVI) where l1=m1=n1=0, or a residue of an aldehyde condensate represented by the formula:

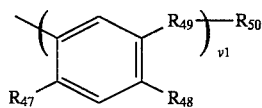

in which $R_{47}$ represents —OH,

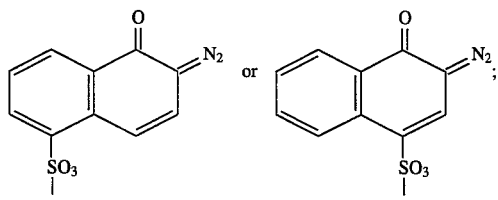

$R_{48}$ represents a substituted or unsubstituted $C_1$ to $C_8$ alkyl group, or a substituted or unsubstituted $C_1$ to $C_8$ alkoxy group; $R_{49}$ represents an aldehyde residue (e.g., residue of formaldehyde, acetaldehyde, propionaldehyde, butylaldehyde, chloroacetaldehyde, or methoxyacetaldehyde); $R_{50}$ represents —H, or a substituted or unsubstituted aromatic residue; and v1 represents an integer of from 1 to 5.

In addition to the above described preferred examples, photosensitive substances obtained by reacting a polyhydroxy compound having at least one group of formula (IV), (V) or (VI) per molecule, a 1,2-naphthoquinonediazidosulfonyl chloride and a dye selected from α-pyrone natural dyes such as bispyrine, diazine natural dyes such as leucoputerin, γ-pyrone natural dyes such as quercetin or rutin, and quinone natural dyes such as alizarin or purpurin, may also be used in the present invention.

Photosensitive substances of formulae (VII) to (XVIII) are obtained by reacting a polyhydroxy compound represented by the formulae (VII') to (XVIII'), respectively, and (a) 1,2-naphthoquinonediazido-5-(and/or -4-)sulfonyl chloride(s) in a mixed solvent comprising an organic solvent and water.

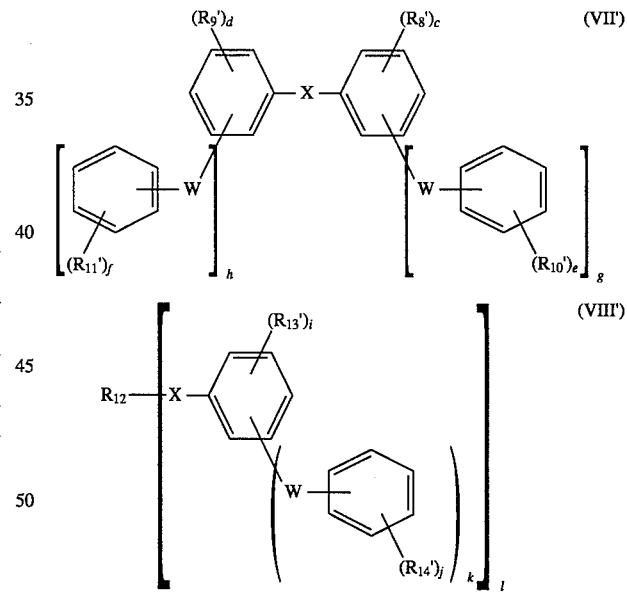

In the above formulae, W represents a linear or branched $C_1$ to $C_6$ alkylene group; X represents a divalent electron attracting group, preferably

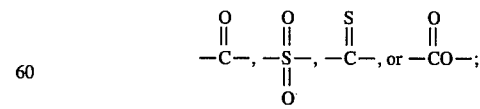

$R_{12}$ represents a $C_1$ to $C_4$ alkane residue, or a $C_6$ to $C_{12}$ aromatic residue; $R'_8$ to $R'_{11}$ and $R'_{13}$ and $R'_{14}$ may be the same or different and each represents —H, —OH, a substituted or unsubstituted $C_1$ to $C_8$ alkyl group, a substituted or unsubstituted $C_1$ to $C_8$ alkoxy group, a substituted or unsubstituted $C_6$ to $C_{15}$ aryl group, a substituted or unsubstituted $C_6$ to $C_{15}$ aralkyl group, a substituted or unsubstituted $C_2$ to $C_{15}$ acyl group, or a substituted or unsubstituted $C_2$ to $C_{15}$ acyloxy group; provided that one molecule of the formula satisfies the condition of $3 \leq \text{—OH} \leq 20$; and c to l are average real numbers which satisfy the following conditions:

c–l: $3 \leq (c + d) \leq 8$
$1 \leq (e + f) \leq 8$
$1 \leq (g + h) \leq 4$
$1 \leq i–l \leq 4$ ,

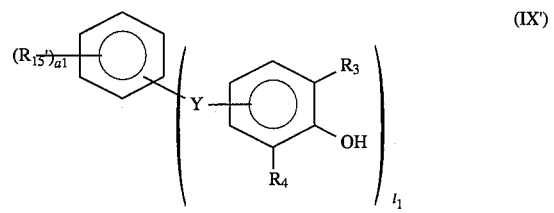
(IX')

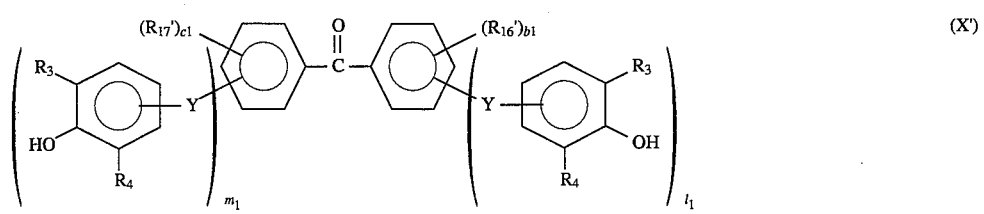
(X')

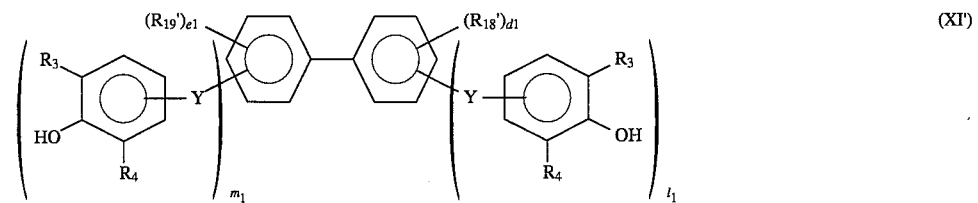
(XI')

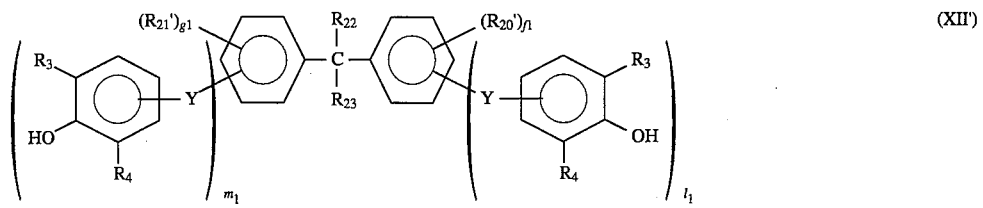
(XII')

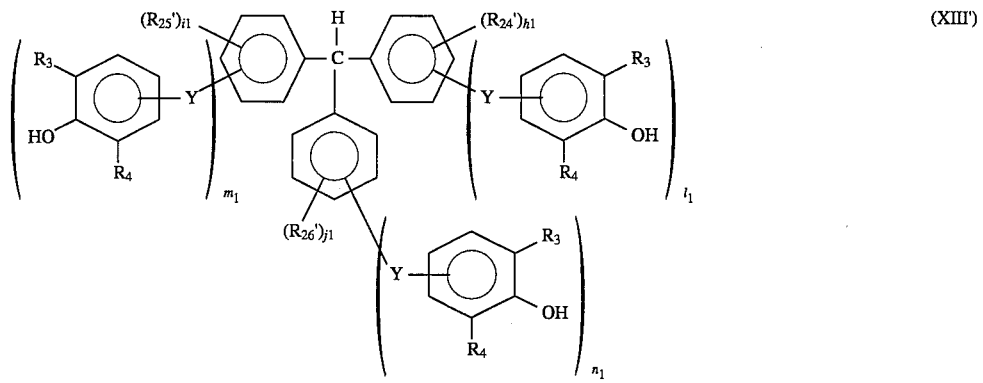
(XIII')

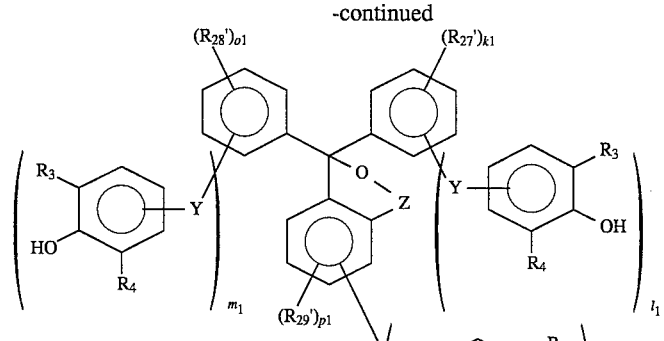

(XIV')

(XV')

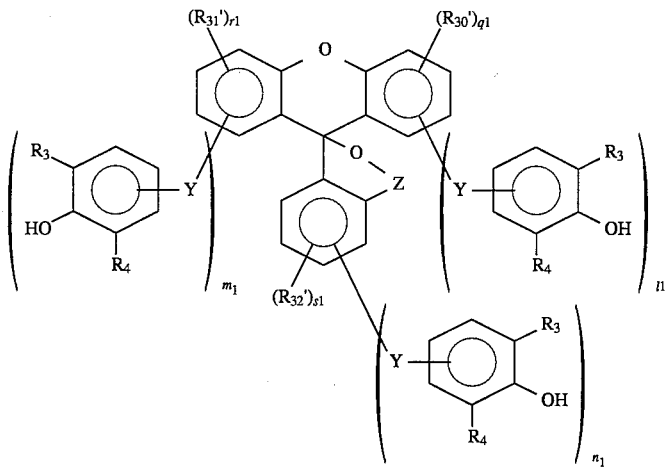

(XVI')

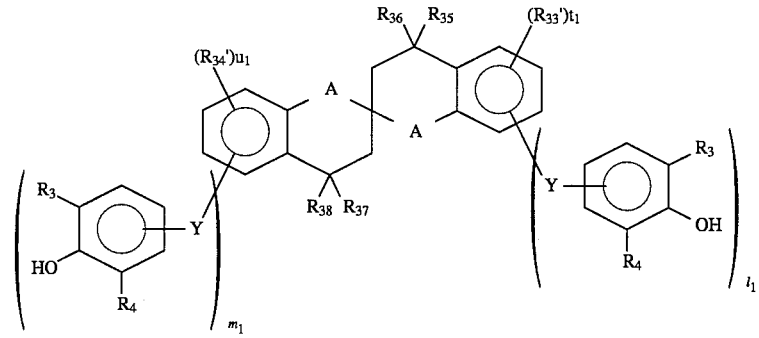

(XVII')

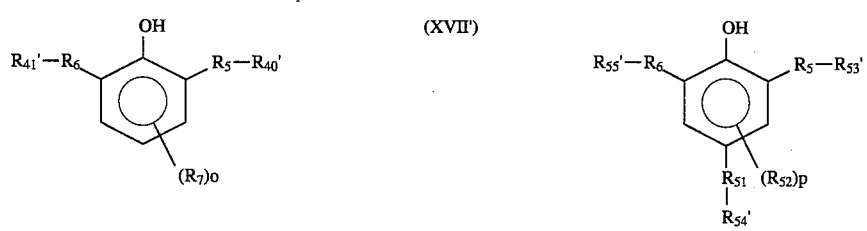

(XVIII')

In the above formulae, $R_3$ and $R_4$ each represent a linear or branched $C_1$ to $C_4$ alkyl or alkoxy group; Y represents a divalent organic group, preferably a linear or branched $C_1$ to $C_4$ alkylene group, $$-\overset{O}{\underset{\|}{C}}-,\ -CO-,\ -\overset{S}{\underset{\|}{C}}-,\ -\overset{O}{\underset{\|}{NHC}}-,\ -\overset{O}{\underset{\|}{NHCO}}-,$$

—S— or —O—, more preferably a linear or branched $C_1$ to $C_4$ alkylene group, $$-\overset{O}{\underset{\|}{C}}-\ \text{or}\ -\overset{O}{\underset{\|}{CO}}-,$$

especially preferably a linear or branched $C_1$ to $C_4$ alkylene group; $R'_{15}$ to $R'_{21}$ and $R'_{24}$ to $R'_{34}$ may be the same or different and each represents —H, —OH, a substituted or unsubstituted $C_1$ to $C_8$ alkyl group, a substituted or unsubstituted $C_1$ to $C_8$ alkoxy group, a substituted or unsubstituted $C_6$ to $C_{15}$ aryl group, a substituted or unsubstituted $C_6$ to $C_{15}$ aralkyl group, a substituted or unsubstituted $C_2$ to $C_{15}$ acyl group, or a substituted or unsubstituted $C_2$ to $C_{15}$ acyloxy group; provided that one molecule of the polyhydroxy compound satisfies the condition of $3 \leq$—OH$\leq 20$; $R_{22}$ and $R_{23}$ each represents —H, —OH, —COOH, —CN, a halogen atom (e.g., F, Cl, Br), —COOR$_{43}$, —R$_{44}$—COOH, —R$_{45}$—COOR$_{46}$ (where $R_{43}$ and $R_{46}$ each represent a substituted or unsubstituted $C_1$ to $C_8$ alkyl group, a substituted or unsubstituted $C_6$ to $C_{15}$ aryl group, or a substituted or unsubstituted $C_6$ to $C_{15}$ aralkyl group; and $R_{44}$ and $R_{45}$ each represents a substituted or unsubstituted $C_1$ to $C_8$ alkylene group, or a substituted or unsubstituted $C_6$ to $C_{15}$ arylene group), a substituted or unsubstituted $C_1$ to $C_8$ alkyl group, a substituted or unsubstituted $C_1$ to $C_8$ alkoxy group, or a substituted or unsubstituted $C_6$ to $C_{15}$ aralkyl group; Z represents —CO— or —SO$_2$—; A represents an oxygen atom or a single bond; a1 to u1 are average real numbers which satisfy the following conditions:

$$a1 \sim u1: \quad 1 \leq a1 \leq 3$$
$$1 \leq l1 \leq 2$$
$$0 \leq m1, n1 \leq 2$$
$$3 \leq \begin{pmatrix} (b1+c1) \\ (d1+e1) \\ (f1+g1) \\ (t1+u1) \end{pmatrix} \leq 7$$
$$3 \leq \begin{pmatrix} (h1+i1+j1) \\ (k1+o1+p1) \\ (q1+r1+s1) \end{pmatrix} \leq 10$$

$R_5$, $R_6$ and $R_{51}$ each represents a linear or branched $C_1$ to $C_4$ alkylene group; $R_{35}$ to $R_{38}$ may be the same or different and each represents —H, —OH, a substituted or unsubstituted $C_1$ to $C_8$ alkyl group, a substituted or unsubstituted $C_1$ to $C_8$ alkoxy group, or a substituted or unsubstituted $C_6$ to $C_{15}$ aralkyl group; $R'_{40}$, $R'_{41}$ and $R'_{54}$ each represents a residue of any one of formulae (IX') to (XVI') where l1=m1=n1=0, or a residue of an aldehyde condensate represented by the formula:

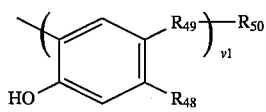

wherein $R_{48}$ represents a substituted or unsubstituted alkyl group, or a substituted or unsubstituted alkoxy group; $R_{49}$ represents an aldehyde residue (e.g., residue of formaldehyde, acetaldehyde, propionaldehyde, butylaldehyde, chloroacetaldehyde, or methoxyacetaldehyde); $R_{50}$ represents —H, or a substituted or unsubstituted aromatic residue; and v1 represents an integer of from 1 to 5.

In addition to the above described preferred examples, other polyhydroxy compounds obtained by introducing at least one group of formula (IV), (V) or (VI) into one molecule of a dye selected from α-pyrone natural dyes such as bispidine, diazine natural dyes such as leucoputerin, γ-pyrone natural dyes such as quercetin or rutin, or quinone natural dyes such as alizarin or purpurin, may also be used in the present invention.

Polyhydroxy compounds having at least one group of formula (II) or (III) per molecule, for example, those of formulae (VII') and (VIII'), and polyhydroxy compounds having at least one group of formula (IV), (V) or (VI), for example, those of formulae (IX') to (XVIII'), are obtained by introducing a group of formula (II), (III), (IV), (V) or (VI) into the base polyhydroxy compound, for example, in accordance with the reactions described below.

Where the base polyhydroxy compound to be reacted has plural active sites, the reaction product is a mixture of compounds reflecting the plural active sites. Such a mixture may also be used in the present invention.

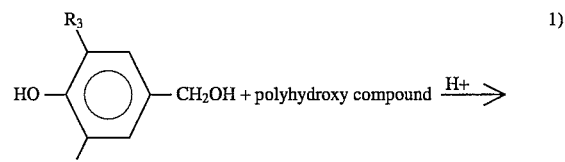

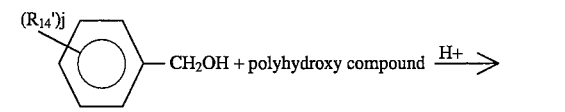

(R" is linear or branched $C_1$ to $C_4$ alkylene group; E is a halogen atom (e.g., F, Cl, Br); $R_3$, $R_4$ and j are as defined above)

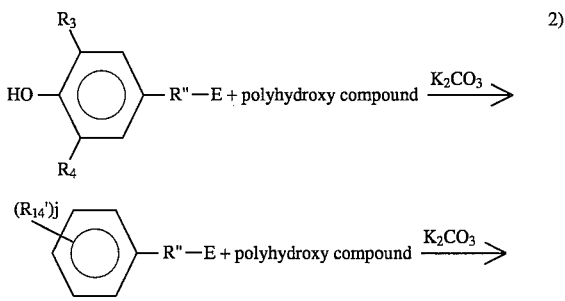

(E is a halogen atom (e.g., F, Cl, Br); G is O or S; and $R_3$, $R_4$ are as defined above)

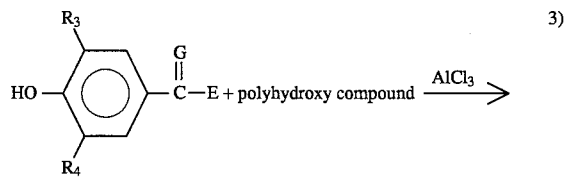

(DBTDL is dibutyl tin dilaurate; and $R_3$ and $R_4$ are as defined above)

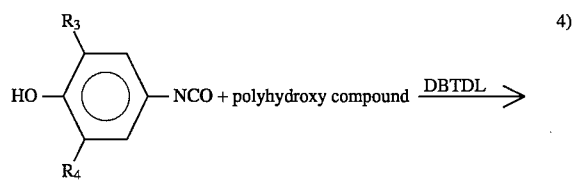

(Polyhydroxy compound is represented by

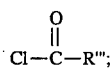

$R'''$ is a polyhydroxy compound residue; and $R_3$ and $R_4$ are as defined above)

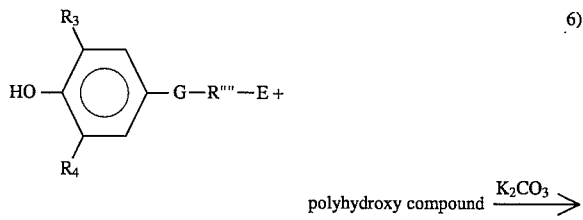

(E is a halogen atom (e.g., F, Cl, Br); G is O or S ; $R''''$ is a linear or branched $C_1$ to $C_4$ alkylene group; and $R_3$ and $R_4$ are as defined above)

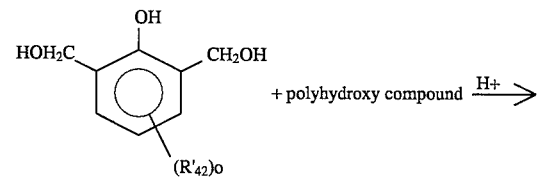

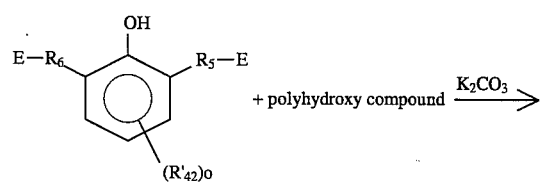

($R_5$ and $R_6$ each are a linear or branched $C_1$ to $C_4$ alkylene group; E is a halogen atom (e.g., F, Cl, Br); $R'_{42}$ and o are as defined above)

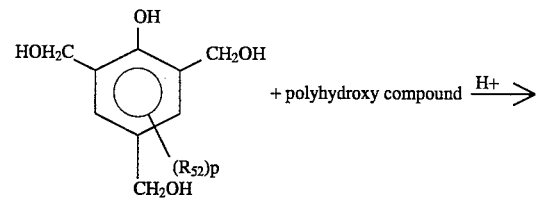

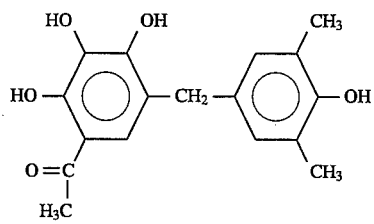

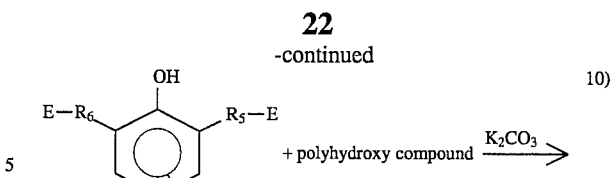

($R_5$, $R_6$ and $R_{51}$ each are a linear or branched $C_1$ to $C_4$ alkylene group; E is a halogen atom (e.g., F, Cl, Br); and $R_{52}$ and p are as defined above)

$R'_8$ to $R'_{11}$, $R'_{13}$ to $R'_{21}$, $R'_{24}$ to $R'_{34}$ and $R'_{40}$ to $R'_{42}$ are described above. Preferably, the groups of $R'_8$ to $R'_{11}$, $R'_{13}$ to $R'_{21}$, $R'_{24}$ to $R'_{34}$ and $R'_{42}$ except —H and —OH, the groups of $R'_{40}$ and $R'_{41}$, and the groups of $R_{22}$ and $R_{23}$ except —H, —OH, —COOH, —CN, halogen, —COOR$_{43}$, —R$_{44}$—COOH and —R$_{45}$—COOR$_{46}$ each are an alkyl or alkoxy group having from 1 to 8 carbon atoms; an aryl or aralkyl group having from 6 to 15 carbon atoms; an alkyl or alkoxy group having from 1 to 8 carbon atoms and substituted by a $C_1$ to $C_8$ alkoxy group, a $C_6$ to $C_{15}$ aryloxy group, a $C_6$ to $C_{15}$ aryl group, a hydroxyl group, a carboxyl group, a sulfonic acid group, an amino group, a nitro group, a silyl group, a silylether group, a cyano group, an aldehyde group, a mercapto group or a halogen atom; an aryl or aralkyl group having from 6 to 15 carbon atoms and substituted by a $C_1$ to $C_8$ alkoxy group, a $C_6$ to $C_{15}$ aryloxy group, a $C_6$ to $C_{15}$ aryl group, a hydroxyl group, a carboxyl group, a sulfone group, an amino group, a nitro group, a silyl group, a silylether group, a cyano group, an aldehyde group, a mercapto group or a halogen atom; or an aliphatic or aromatic acyl or acyloxy group having from 2 to 15 carbon atoms.

Preferred examples of the polyhydroxy compound for use in the present invention are described above. More preferred examples of the polyhydroxy compound are described below.

The photoresist composition of the present invention contains a photosensitive substance that may be obtained by esterifying a mixture of polyhydroxy compounds as a starting material, and exhibits the same excellent effect as that of a composition containing a photosensitive substance derived from a single polyhydroxy compound, provided that the esterified mixture satisfies the above described esterification conditions.

Particularly preferred examples of the polyhydroxy compound for use in the present invention are set forth below.

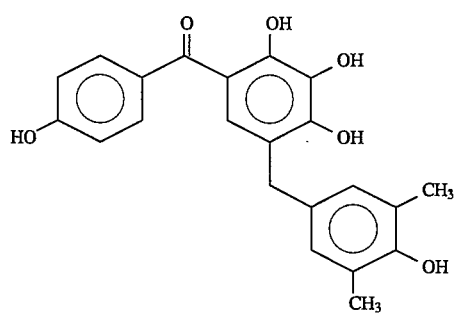

P-3 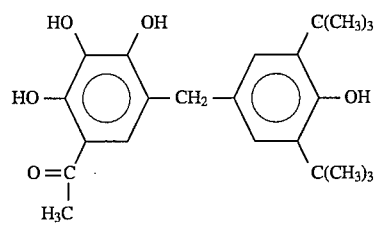
P-4 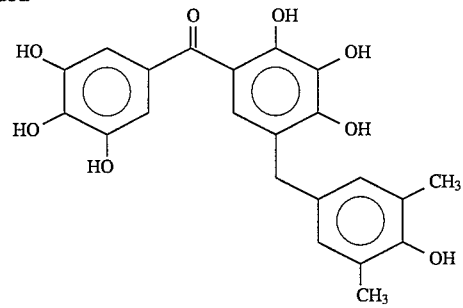
P-5 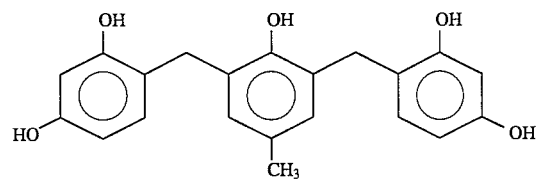
P-6 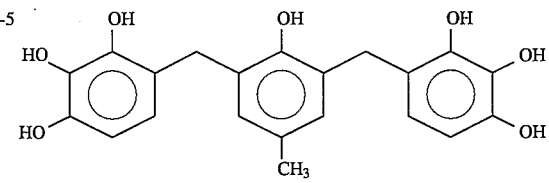
P-7 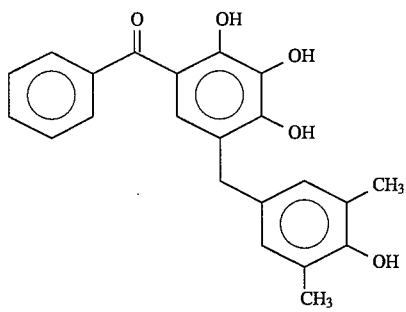
P-8 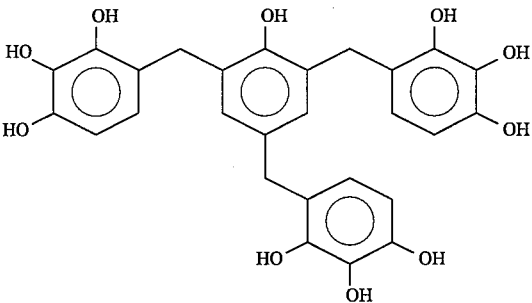
P-9 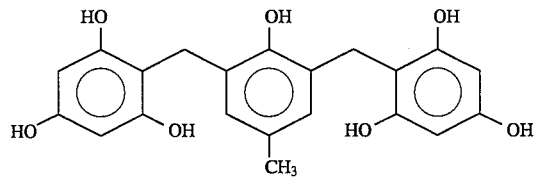
P-10 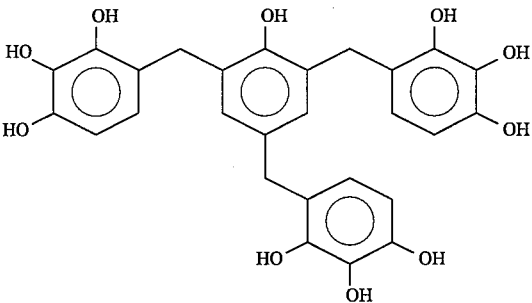
P-11 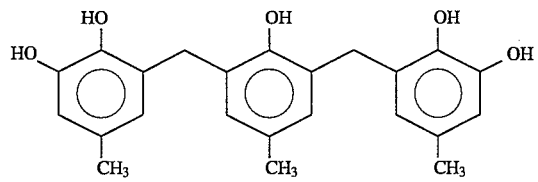
P-13 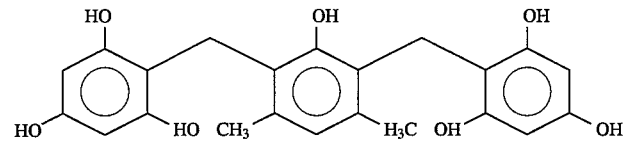

P-14
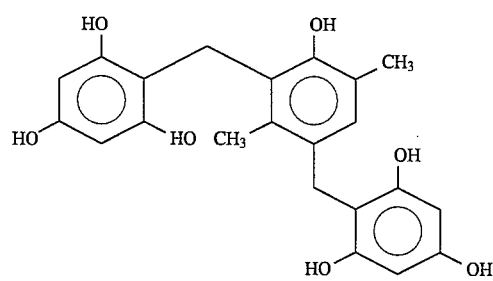
P-15
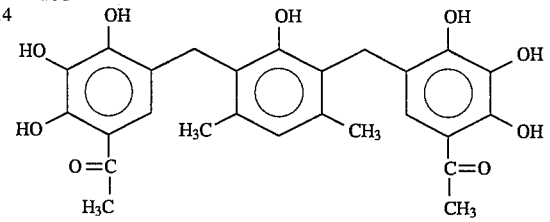
P-16
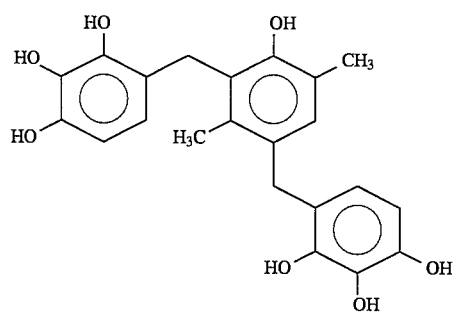
P-17
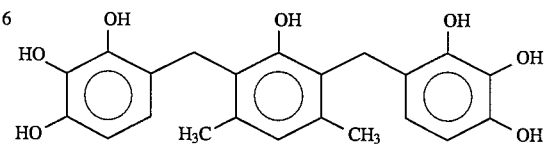
P-18
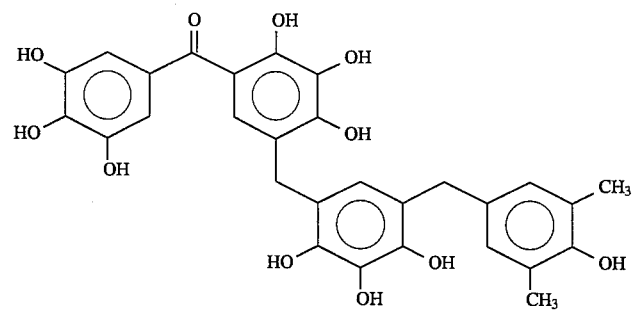
P-19
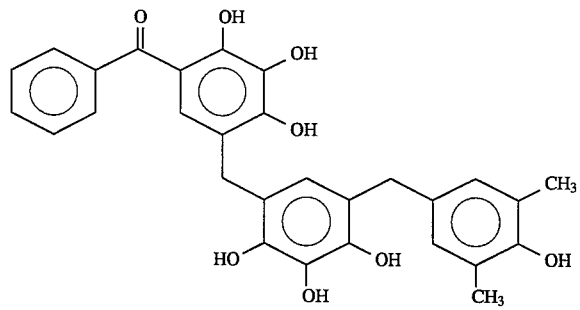
P-20
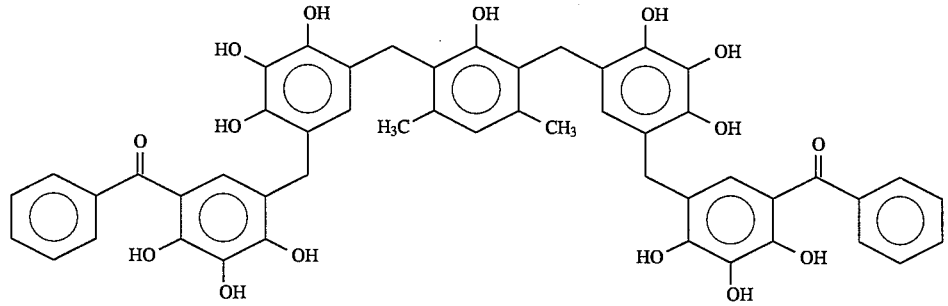

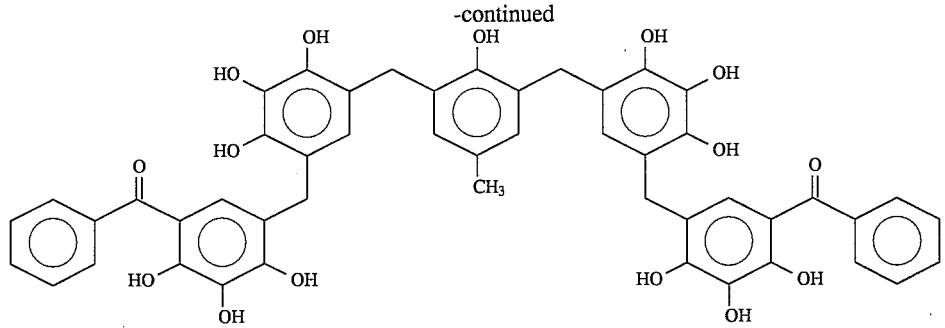

P-21

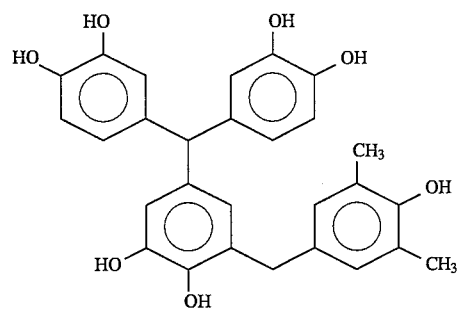

P-22

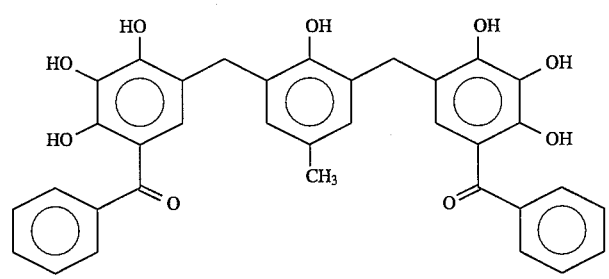

P-23

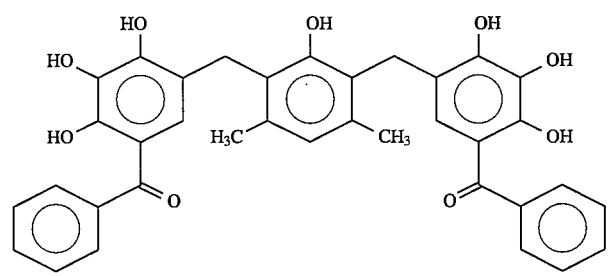

P-24

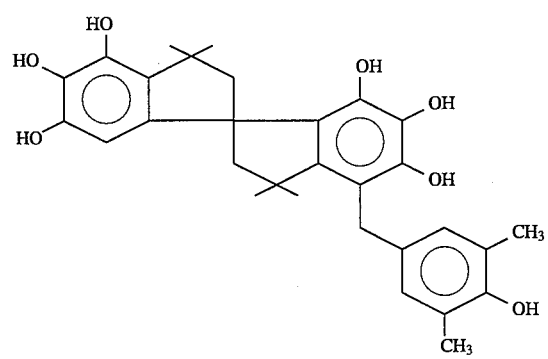

P-25

Esterification of a polyhydroxy compound of any of formulae (VII') to (XVIII') and (a) 1,2-naphthoquinonediazido-5-(and/or -4-) sulfonyl chloride(s) is carried out as described below.

A predetermined amount of a polyhydroxy compound of any of formulae (VII') to (XVIII'), a predetermined amount of one or more 1,2-naphthoquinonediazido-5-(and/or -4-) sulfonyl chloride(s) and a predetermined amount of a mixed solvent comprising an organic solvent and water are placed in a flask, and condensation of the reactants is effected with dropwise adding a basic catalyst such as sodium hydroxide, sodium carbonate, sodium hydrogencarbonate or triethylamine thereto. The organic solvent is preferably dioxane, acetone, methyl ethyl ketone, N-methylpyrrolidone or γ-butyrolactone. More preferably, N-methylpyrrolidone or γ-butyrolactone is selectively used. In order to enhance selectivity of the reaction as intended by the present invention, the mixing ratio of the mixed solvent of organic solvent/water for use in the esterification reaction is important. Preferably the mixing ratio of organic solvent/water is from 100/5 to 100/100, more preferably from 100/10 to 100/50, most preferably from 100/15 to 100/43, by volume.

The product thus obtained is washed with water, purified and dried. In accordance with the above described method, for example, photosensitive substances of formulae (IX) to (XVIII) may be prepared.

Alkali-soluble novolak resins for use in the present invention are obtained by reacting one mol of a phenol compound and from 0.6 to 1.0 mol of an aldehyde compound by addition condensation in the presence of an acidic catalyst. Useful phenol compounds include phenol, o-cresol, m-cresol, p-cresol and xylenol. These phenol compounds may be used alone or in combination of two or more. Useful aldehyde compounds include formaldehyde, paraformaldehyde, acetaldehyde, halogenated acetaldehydes (e.g., chloroacetaldehyde, bromoacetaldehyde) and furfural. Useful acidic catalysts include hydrochloric acid, sulfuric acid, formic acid, oxalic acid and acetic acid. Novolak resins thus obtained, having a molecular weight of from 1,000 to 50,000, are soluble in alkali substances.

In the composition of the present invention, the proportion of the photosensitive substance to the alkali-soluble novolak resin is such that the content of the photosensitive substance is from 5 to 100 parts by weight, preferably from 10 to 50 parts by weight, per 100 parts by weight of the novolak resin. If the content of the photosensitive substance is less than 5 parts by weight, the film retentiveness is too low. On the contrary, if the content of the photosensitive substance is more than 100 parts by weight, the sensitivity of the composition is low and the solubility thereof in solvents is also reduced.

The composition of the present invention essentially contains the above described photosensitive substance, but, if desired, may additionally contain known photosensitive substances such as the esterified products of 2,3,4-trihydroxybenzophenone, 2,4,4'-trihydroxybenzophenone or 2,4,6-trihydroxybenzophenone and 1,2-naphthoquinonediazido-5- (and/or -4-)sulfonyl chloride(s). In this case, the content of the additional photosensitive substances is 100 parts by weight or less, preferably 30 parts by weight or less, to 100 parts by weight of the photosensitive substance of the present invention, for example, those of the above described formulae (IX) to (XVIII). Furthermore, the composition of the present invention can contain a polyhydroxy compound in order to enhance the solubility of the composition in a developer. Preferred examples of polyhydroxy compounds useful for this purpose include phenols, resorcinol, phloroglucinol, 2,3,4-trihydroxybenzophenone, 2,3,4,4'-tetrahydroxybenzophenone, 2,3,4,3',4',5'-hexahydroxybenzophenone, and acetone-pyrogallol condensate resin.

Useful examples of solvents which dissolve the photosensitive substances and alkali-soluble novolak resins of the present invention to prepare coating solutions include ketones such as methyl ethyl ketone and cyclohexanone; alcohol ethers such as ethylene glycol monomethyl ether and ethylene glycol monoethyl ether; ethers such as dioxane and ethylene glycol dimethyl ether; cellosolve esters such as methyl cellosolve acetate and ethyl cellosolve acetate; fatty acid esters such as methyl lactate, ethyl lactate and butyl acetate; halogenated hydrocarbons such as 1,1,2-trichloroethylene; and high polar solvents such as dimethylacetamide, N-methylpyrrolidone, dimethylformamide and dimethyl sulfoxide. These solvents can be used alone or in combination of two or more.

The positive photoresist composition of the present invention can contain, as desired, commonly employed dyes, plasticizers, adhesive aids and surfactants as an additive. Specific examples of such additives are dyes such as methyl violet, crystal violet and malachite green; plasticizers such as stearic acid, acetal resins, phenoxy resins and alkyd resins; adhesive aids such as hexamethyldisilazane and chloromethylsilane; and surfactants such as nonylphenoxy-poly(ethyleneoxy)ethanol and octylphenoxy-poly(ethyleneoxy)ethanol.

The positive photoresist composition of the present invention is coated on a substrate which is generally used in the manufacture of precision integrated circuit elements (for example, silicon/silicon dioxide-coated substrate) with a spinner or coater, exposed through a defined pattern mask and then developed to provide a resist pattern meeting the above noted objectives of the present invention.

As a developer for use for developing the positive photoresist composition of the present invention, an aqueous solution of an alkali substance, for example, inorganic alkali substances such as sodium hydroxide, potassium hydroxide, sodium carbonate, sodium silicate, sodium metasilicate or aqueous ammonia; primary amines such as ethyl amine or n-propylamine; secondary amines such as diethylamine or di-n-butylamine; tertiary amines such as triethylamine or methyldiethylamine; alcoholamines such as dimethylethanolamine or triethanolamine; quaternary ammonium salts such as tetramethylammonium hydroxide or tetraethylammonium hydroxide; or cyclic amines such as pyrrole or piperidine, can be used. Additionally, the aqueous alkaline solution may further contain desired amounts of alcohols and surfactants.

The positive photoresist of the present invention is suitable for exposure with g-ray, i-ray and excimer laser (248 nm) and has high sensitivity, high resolving power and precise reproducibility to provide resist images having good sectional shapes, broad development latitude, high heat-resistance and good storage stability.

Next, the present invention will be explained in more detail by way of the following examples, which, however, are not intended to restrict the scope of the present invention. In the following examples, "%" is by weight, unless otherwise specifically indicated.

SYNTHESIS EXAMPLES (1) Synthesis of Photosensitive Substance (a):

10 g of the following compound (a'):

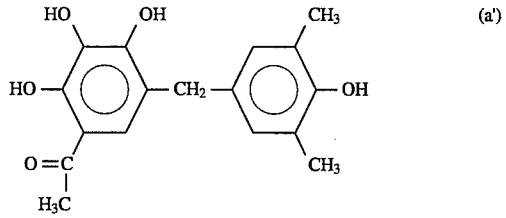

(a')

27.0 g of 1,2-naphthoquinonediazido-5-sulfonyl chloride and a mixed solvent of acetone/water (300 ml/75 ml) were placed in a three-neck flask and dissolved uniformly. Next, a mixed liquid of triethylamine/acetone (10.7 g/45 ml) was gradually and dropwise added thereto and the mixture was reacted for 3 hours at 25° C. The reaction mixture was then poured into 1,400 ml of an aqueous 1% hydrochloric acid solution, whereupon the precipitate formed was removed by filtration. The filtered precipitate was washed with water and dried at 40° C., to obtain 28.5 g of a photosensitive substance containing 87 wt % of a component having the following structure.

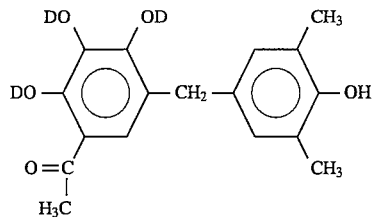

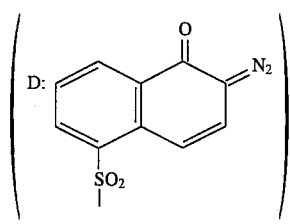

(2) Synthesis of Photosensitive Substance (b):

10 g of the following compound (b'):

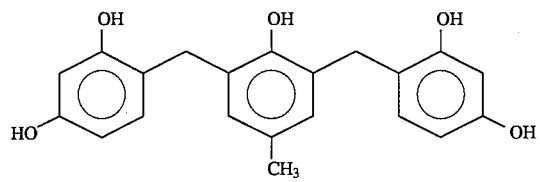

31.3 g of 1,2-naphthoquinonediazido-5-sulfonyl chloride and a mixed solvent of γ-butyrolactone/water (300 ml/75 ml) were placed in a three-neck flask and dissolved uniformly. Next, a mixed liquid of triethylamine/acetone (12.4 g/55 ml) was gradually and dropwise added thereto and reacted for 3 hours at 25° C. The reaction mixture was then poured into 1,600 ml of an aqueous 1% hydrochloric acid solution, whereupon the precipitate formed was removed by filtration. The filtered precipitate was washed with water and dried at 40° C., to obtain 31 g of a photosensitive substance containing 71 wt % of a component having the following structure.

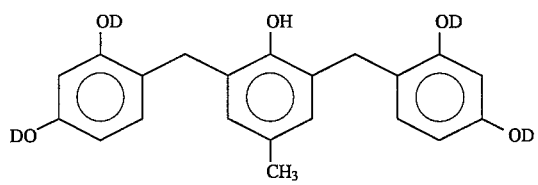

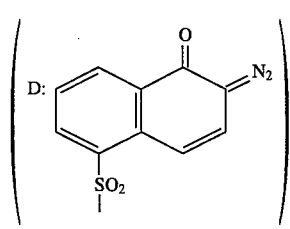

(3) Synthesis of Photosensitive Substance (c):

10 g of the following compound (c'):

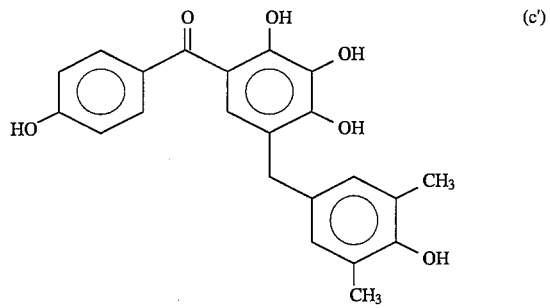

21.2 g of 1,2-naphthoquinonediazido-5-sulfonyl chloride and a mixed solvent of acetone/water (240 ml/80 ml) were placed in a three-neck flask and dissolved uniformly. Next, a mixed liquid of 4-dimethylaminopyridine/acetone (10.1 g/115 ml) was gradually and dropwise added thereto and reacted for 3 hours at 25° C. The reaction mixture was then poured into 1,000 ml of an aqueous 1% hydrochloric acid solution, whereupon the precipitate formed was removed by filtration. The filtered precipitate was washed with water and dried at 40° C., to obtain 25 g of a photosensitive substance containing 75 wt % of a component having the following structure.

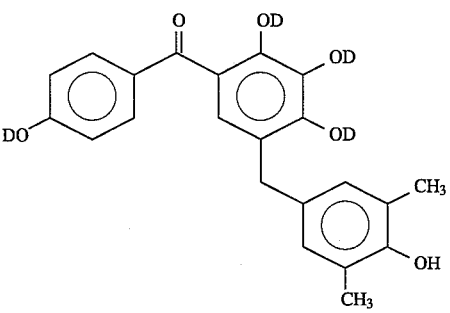

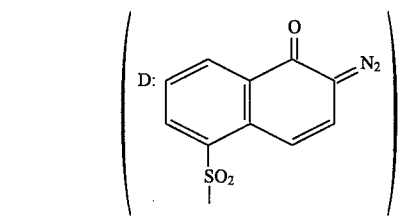

(4) Synthesis of Photosensitive Substance (d):

10 g of the following compound (d'):

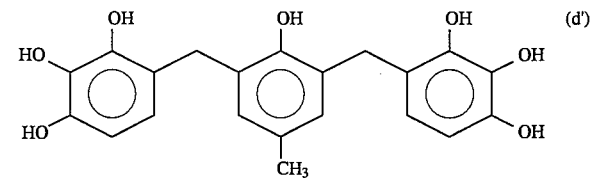

42.0 g of 1,2-naphthoquinonediazido-5-sulfonyl chloride and a mixed solvent of γ-butyrolactone/water (400 ml/100 ml) were placed in a three-neck flask and dissolved uniformly. Next, a mixed liquid of 4-dimethylaminopyridine/ acetone (20.1 g/230 ml) was gradually and dropwise added thereto and reacted for 3 hours at 25° C. The reaction mixture was then poured into 3,200 ml of an aqueous 1% hydrochloric acid solution, whereupon the precipitate formed was removed by filtration. The filtered precipitate was washed with water and dried at 40° C., to obtain 41.5 g of a photosensitive substance containing 55 wt %% of a component having the following structure.

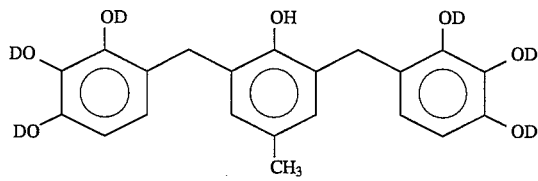

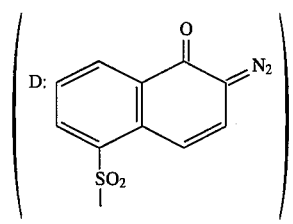

(5) Synthesis of Photosensitive Substance (e):

10 g of the following compound (d'):

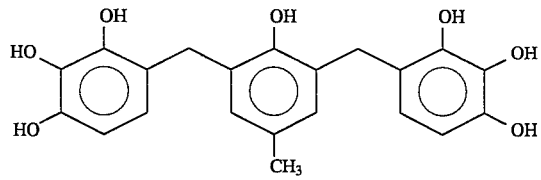

49.0 g of 1,2-naphthoquinonediazido-5-sulfonyl chloride and a mixed solvent of γ-butyrolactone/water (465 ml/120 ml) were placed in a three-neck flask and dissolved uniformly. Next, a mixed liquid of 4-dimethylaminopyridine/ acetone (23.4 g/270 ml) was gradually and dropwise added thereto and reacted for 3 hours at 25° C. The reaction mixture was then poured into 3,700 ml of an aqueous 1% hydrochloric acid solution, whereupon the precipitate formed was removed by filtration. The filtered precipitate was washed with water and then with methanol and dried at 40° C., to obtain 44.0 g of a photosensitive substance containing 81 wt % of a component having the following structure.

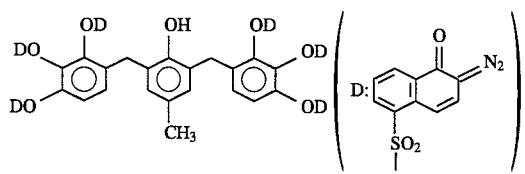

(6) Synthesis of Photosensitive Substance (f):

10 g of the following compound (f'):

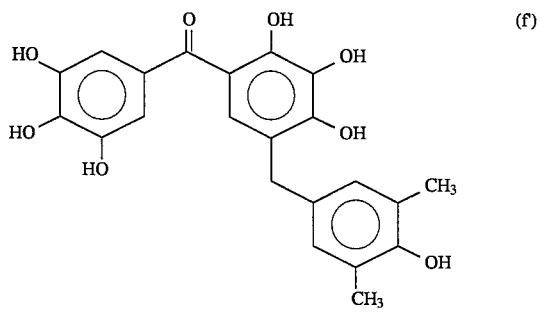

40.4 g of 1,2-naphthoquinonediazido-5-sulfonyl chloride and a mixed solvent of γ-butyrolactone/water (380 ml/125 ml) were placed in a three-neck flask and dissolved uniformly. Next, a mixed liquid of 4-dimethylaminopyridine/ acetone (19.3 g/220 ml) was gradually and dropwise added thereto and reacted for 3 hours at 25° C. The reaction mixture was poured into 3,200 ml of an aqueous 1% hydrochloric acid solution, whereupon the precipitate formed was removed by filtration. The filtered precipitate was washed with water and then with methanol and dried at 40° C., to obtain 38.1 g of a photosensitive substance containing 91 wt % of a component having the following structure.

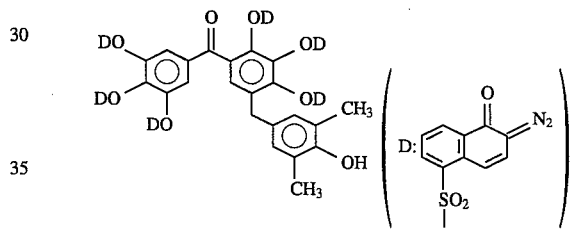

(7) Synthesis of Photosensitive Substance (g):

10 g of the following compound (g'):

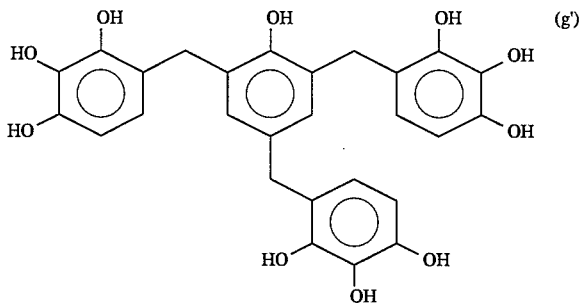

49.3 g of 1,2-naphthoquinonediazido-5-sulfonyl chloride and a mixed solvent of γ-butyrolactone/water (470 ml/135 ml) were placed in a three-neck flask and dissolved uniformly. Next, a mixed liquid of 4-dimethylaminopyridine/ acetone (24.0 g/280 ml) was gradually and dropwise added thereto and reacted for 3 hours at 25° C. The reaction mixture was poured into 4,500 ml of an aqueous 1% hydrochloric acid solution, whereupon the precipitate formed was removed by filtration. The filtered precipitate was washed with water and dried at 40° C., to obtain 43.1 g of a photosensitive substance containing 62 wt % of a component having the following structure.

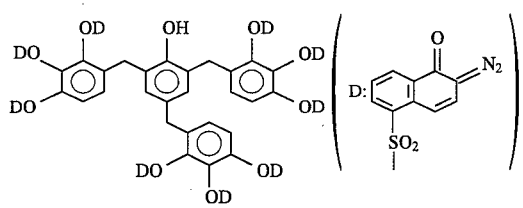

(8) Synthesis of Photosensitive Substance (h):

10 g of the following compound (h'):

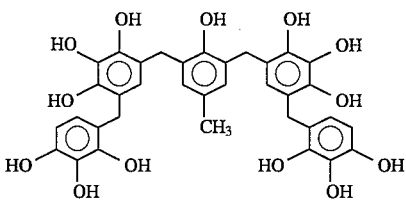

48.9 g of 1,2-naphthoquinonediazido-5-sulfonyl chloride and a mixed solvent of γ-butyrolactone/water (470 ml/90 ml) were placed in a three-neck flask and dissolved uniformly. Next, a mixed liquid of 4-dimethylaminopyridine/acetone (23.8 g/275 ml) was gradually and dropwise added thereto and reacted for 3 hours at 25° C. The reaction mixture was then poured into 4,000 ml of an aqueous 1% hydrochloric acid solution, whereupon the precipitate formed was removed by filtration. The filtered precipitate was washed with water and dried at 40° C., to obtain 44.1 g of a photosensitive substance containing 73 wt % of a component having the following structure.

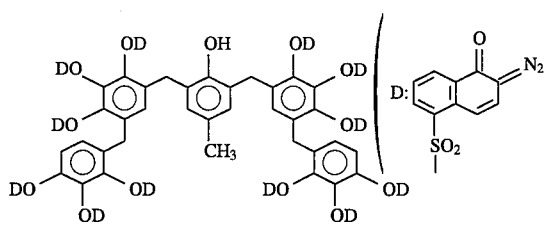

(9) Synthesis of Photosensitive Substance (i):

10 g of the following compound (i'):

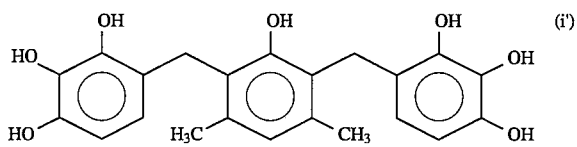

40.7 g of 1,2-naphthoquinonediazido-5-sulfonyl chloride and a mixed solvent of γ-butyrolactone/water (390 ml/130 ml) were placed in a three-neck flask and dissolved uniformly. Next, a mixed liquid of 4-dimethylaminopyridine/acetone (19.8 g/230 ml) was gradually and dropwise added thereto and reacted for 3 hours at 25° C. The reaction mixture was then poured into 4,500 ml of an aqueous 1% hydrochloric acid solution, whereupon the precipitate formed was removed by filtration. The filtered precipitate was washed with water and dried at 40° C., to obtain 39 g of a photosensitive substance containing 77 wt % of a component having the following structure.

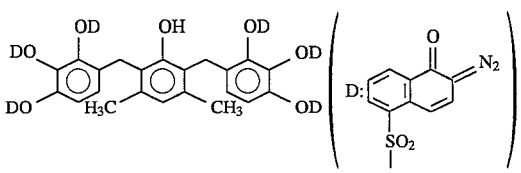

(10) Synthesis of Photosensitive Substance (j):

10 g of the following compound (j'):

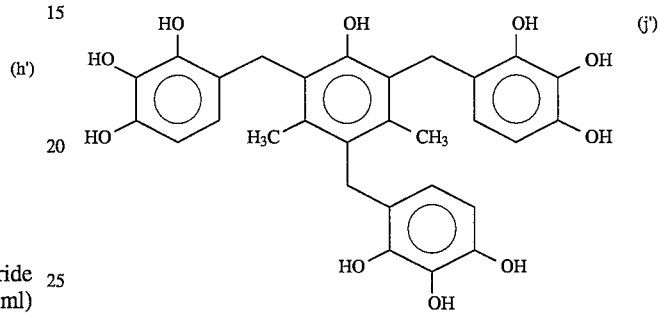

45.2 g of 1,2-naphthoquinonediazido-5-sulfonyl chloride and a mixed solvent of γ-butyrolactone/water (430 ml/108 ml) were placed in a three-neck flask and dissolved uniformly. Next, a mixed liquid of 4-dimethylaminopyridine/acetone (21.6 g/250 ml) was gradually and dropwise added thereto and reacted for 3 hours. The reaction mixture was then poured into 4,000 ml of an aqueous 1% hydrochloric acid solution, whereupon the precipitate formed was removed by filtration. The filtered precipitate was washed with water and dried at 40° C., to obtain 40.8 g of a photosensitive substance containing 71 wt % of a component having the following structure.

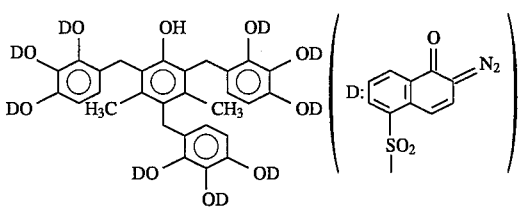

(11) Synthesis of Photosensitive Substance (k):

10 g of the following compound (k'):

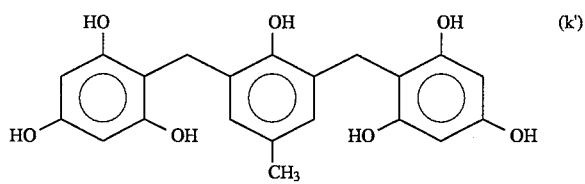

42.7 g of 1,2-naphthoquinonediazido-5-sulfonyl chloride and a mixed solvent of γ-butyrolactone/water (400 ml/100 ml) were placed in a three-neck flask and dissolved uniformly. Next, a mixed liquid of 4-dimethylaminopyridine/acetone (20.8 g/250 ml) was gradually and dropwise added thereto and reacted for 3 hours at 25° C. The reaction mixture was then poured into 3,800 ml of an aqueous 1% hydrochloric acid solution, whereupon the precipitate formed was removed by filtration. The filtered precipitate was washed with water and dried at 40° C., to obtain 39.0 g of a photosensitive substance containing 67 wt % of a component having the following structure.

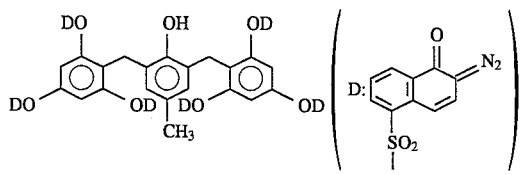

(12) Synthesis of Photosensitive Substance (l):

10 g of the following compound (l'):

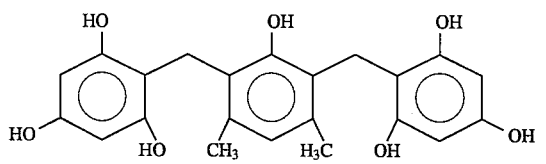

40.5 g of 1,2-naphthoquinonediazido-5-sulfonyl chloride and a mixed solvent of γ-butyrolactone/water (400 ml/ 140 ml) were placed in a three-neck flask and dissolved uniformly. Next, a mixed liquid of 4-dimethylaminopyridine/ acetone (19.3 g/220 ml) was gradually and dropwise added thereto and reacted for 3 hours at 25° C. The reaction mixture was poured into 4,500 ml of an aqueous 1% hydrochloric acid solution, whereupon the precipitate formed was removed by filtration. The filtered precipitate was washed with water and dried at 40° C., to obtain 38.4 g of a photosensitive substance containing 74 wt % of a component having the following structure.

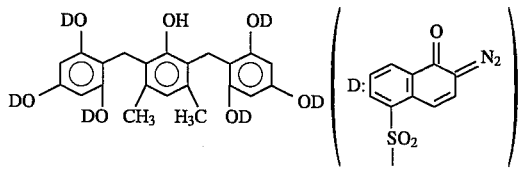

(13) Synthesis of Photosensitive Substance (m):

As a comparative example, a photosensitive substance (m) was prepared. 10 g of the following compound (m'):

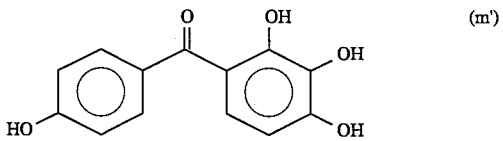

30.0 g of 1,2-naphthoquinonediazido-5-sulfonyl chloride and 340 ml of acetone were placed in a three-neck flask and dissolved uniformly. Next, a mixed liquid of triethylamine/ acetone (11.9 g/50 ml) was gradually and dropwise added thereto and reacted for 3 hours at 25° C. The reaction mixture was then poured into 2,000 ml of an aqueous 1% hydrochloric acid solution, whereupon the precipitate formed was removed by filtration. The filtered precipitate was washed with water and dried at 40° C., to obtain 32.8 g of the 1,2-naphthoquinonediazido- 5-sulfonate of compound (m').

(14) Synthesis of Photosensitive Substance (n):

As a second comparative example, a photosensitive substance (n) was prepared. 10 g of the above noted compound (m'), 48.1 g of 1,2-naphthoquinonediazido-5-sulfonyl chloride and 550 ml of acetone were placed in a three-neck flask and dissolved uniformly. Next, a mixed liquid of triethylamine/acetone (19.0 g/80 ml) was gradually and dropwise added thereto and reacted for 3 hours at 25° C. The reaction mixture was then poured into 3,300 ml of an aqueous 1% hydrochloric acid solution, whereupon the precipitate formed was removed by filtration. The filtered precipitate was washed with water and then with methanol and dried, to obtain 46.0 g of the 1,2-naphthoquinonediazido-5-sulfonate of compound (m').

(15) Synthesis of Novolak Resin:

37 g of m-cresol, 63 g of p-cresol, 51.0 g of 37 wt % formalin and 0.05 g of oxalic acid were placed in a three-neck flask, heated to 100° C. with stirring and reacted for 7 hours. After reaction, the reaction mixture was cooled to room temperature and the inner pressure in the flask was reduced to 30 mm Hg. Next, the content of the flask was gradually heated to 150° C., whereupon water and the nonreacted monomers were removed. The thus obtained novolak resin had a weight average molecular weight of 7,500 (as polystyrene).

EXAMPLES 1 TO 12 AND COMPARATIVE EXAMPLES 1 AND 2

Preparation of Positive Photoresist Compositions and Evaluation Thereof:

Characteristic properties of photosensitive substances (a) to (n) as prepared in the above Synthesis Examples (1) to (14) are shown in Table 1 below.

1.10 g of each of the substances (a) to (n) and 5 g of the cresol novolak resin (molecular weight: 7,500) obtained in Synthesis Example (15) were dissolved in 18 g of ethyl cellosolve acetate and then filtered through a 0.2 μm microfilter to prepare a photoresist composition. The thus prepared photoresist composition was coated onto a silicon wafer with a spin coater and dried in a convection current oven having a nitrogen atmosphere, at 110° C. for 30 minutes to form a resist film having a thickness of 1.2 μm. The film was then exposed by the use of a reduction projection exposure device (NSR1505, manufactured by Nikon Co.) and developed with an aqueous 2.38% tetramethylammonium hydroxide solution for 1 minute. The silicon wafer having the developed resist image thereon was rinsed with water for 30 seconds and dried. The resist pattern was observed with a scanning electron microscope to evaluate the properties of the resist. The results obtained are shown in Table 2 below.

The sensitivity is defined as the reciprocal of the exposure amount to reproduce a mask pattern of 1.0 μm, and was represented as a relative value to the sensitivity value of the control sample of Comparative Example 2.

The film retentiveness is represented by the percentage of the ratio of the nonexposed part before development to that after development.

The resolving power is the critical resolving power for the exposure amount of reproducing a mask pattern of 1.0 μm.

To evaluate the heat resistance, the resist pattern-formed silicon wafer was baked in a convection current oven for 30 minutes, and the temperature at which the pattern did not deform (i.e., flow) under the baking condition upon microscopic inspection is referred to as the heat-resistance.

The shape of the resist is represented by the angle (θ) formed by the surface of the resist wall and the plane surface of the silicon wafer, for a cross section of a resist pattern of 1.0 μm.

From the results shown in Table 2, it is clearly seen that the resists formed from the photosensitive substances (a) to (l) of the present invention exhibited remarkably excellent resolving power and resist shape. Additionally, the photosensitive substances of the present invention have a high solubility in ethyl cellosolve acetate. The resist compositions containing the photosensitive substances of the present invention were stable for a long period of time, and no precipitate was formed therein even after storage for 30 days at 40° C. On the other hand, the resist composition solutions containing comparative photosensitive substances (m) and (n) were unstable and formed precipitates after storage under the same conditions.

TABLE 1

Characteristic Properties of Photosensitive Substance

| Example No. | Photosensitive Substance | Proportion (wt %) of Components Having One —OH Group per Molecule in the Photosensitive Substance | Proportion (wt %) of Complete Ester Component Molecules in the Photosensitive Substance |
| --- | --- | --- | --- |
| Example 1 | a | 87 | 5 |
| Example 2 | b | 71 | 10 |
| Example 3 | c | 75 | 12 |
| Example 4 | d | 55 | 18 |
| Example 5 | e | 81 | 11 |
| Example 6 | f | 91 | 4 |
| Example 7 | g | 62 | 11 |
| Example 8 | h | 73 | 10 |
| Example 9 | i | 77 | 7 |
| Example 10 | j | 71 | 14 |
| Example 11 | k | 67 | 12 |
| Example 12 | l | 74 | 11 |
| Comparative Example 1 | m | 30 | 45 |
| Comparative Example 2 | n | 0 | 100 |

While the invention has been described in detail and with reference to specific embodiments thereof, it will be apparent to one skilled in the art that various changes and modifications can be made therein without departing from the spirit and scope thereof.

What is claimed is:

1. A positive photoresist composition containing an alkali-soluble resin and a photosensitive substance in admixture, the photosensitive substance is contained in the photoresist composition in an amount of from 5 to 100 parts by weight per 100 parts by weight of the alkali-soluble resin, the photosensitive substance is obtained by reaction of a polyhydroxy compound and a 1,2-naphthoquinone-diazido-5-(and/or -4-)sulfonyl chloride, said photosensitive substance being a mixture of compounds (1) to (3):

(1) a photosensitive compound having at least one hydroxyl group per molecule and having a number ratio of 1,2-naphthoquinonediazido-5-(and/or -4-) sulfonyl chloride sulfonate groups to hydroxyl groups within the range of from 3 to 20, said compound (1) contained in the photosensitive substance in an amount of 50 wt % or more;

(2) a photosensitive compound where all the hydroxyl groups in the polyhydroxy compound have been 1,2-naphthoquinonediazidosulfonyl-esterified, said compound (2) contained in the photosensitive substance in an amount of 30 wt % to 0 wt %; and (3) a compound having three or more hydroxyl groups which have not been 1,2-naphthoquinonediazidosulfonyl-esterified per molecule, said compound (3) contained in the photosensitive substance in an amount of 20 wt % to 0 wt %.

2. A positive photoresist composition as in claim 1, wherein the photosensitive substance is a mixture of the compounds (1) to (3) below obtained by reaction of a polyhydroxy compound and a 1,2-naphthoquinonediazido-5-(and/or -4- ) sulfonyl chlorides represented by formula (I):

TABLE 2

Results of Evaluation

| Example No. | Photosensitive Substance | Relative Sensitivity | Film Retentiveness (%) | Resolving Power (μm) | Heat-Resistance (°C.) | Shape of Resist (θ) |
| --- | --- | --- | --- | --- | --- | --- |
| Example 1 | a | 1.6 | 99 | 0.65 | 135 | 89 |
| Example 2 | b | 1.3 | 99 | 0.65 | 135 | 88 |
| Example 3 | c | 1.2 | 99 | 0.65 | 130 | 89 |
| Example 4 | d | 1.4 | 98 | 0.70 | 130 | 88 |
| Example 5 | e | 1.5 | 100 | 0.65 | 140 | 89 |
| Example 6 | f | 1.6 | 100 | 0.65 | 145 | 89 |
| Example 7 | g | 1.3 | 100 | 0.65 | 145 | 89 |
| Example 8 | h | 1.2 | 100 | 0.65 | 140 | 89 |
| Example 9 | i | 1.5 | 100 | 0.65 | 145 | 89 |
| Example 10 | j | 1.3 | 100 | 0.65 | 150 | 89 |
| Example 11 | k | 1.5 | 100 | 0.65 | 140 | 89 |
| Example 12 | l | 1.5 | 100 | 0.65 | 145 | 89 |
| Comparative Example 1 | m | 1.2 | 97 | 0.80 | 120 | 83 |
| Comparative Example 2 | n | 1.0 | 100 | 0.75 | 130 | 85 |

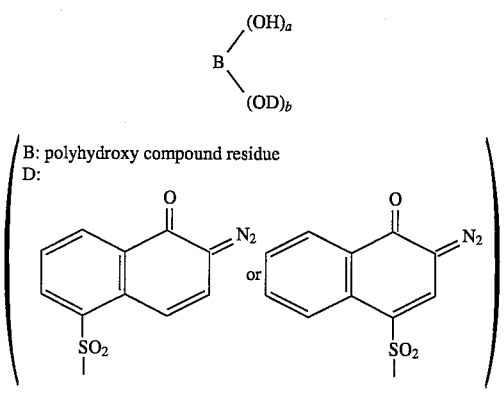

(1) $1 \leq a \leq 2$, and $b/a = 3/1$ to $20/1$ (number ratio), contained in the photosensitive substance in an amount of 50 wt % or more;

(2) $a=0$, and $1 \leq b$ (complete ester), contained in the photosensitive substance in an amount of 30 wt % to 0 wt %; and (3) $3 \leq a$, and $0 \leq b$, contained in the photosensitive substance in an amount of 20 wt % to 0 wt %.

3. A positive photoresist composition as in claim 2, wherein a is 1 and b/a is from 4/1 to 12/1 in the compound (1).

4. A positive photoresist composition as in claim 2, wherein compound (1) is contained in the photosensitive substance in an amount of 60 wt % or more.

5. A positive photoresist composition as in claim 2, wherein compound (2) is contained in the photosensitive substance in an amount of 20 wt % to 0 wt %.

6. A positive photoresist composition as in claim 2, wherein compound (3) is contained in the photosensitive substance in an amount of 15 wt % to 0 wt %.

7. A positive photoresist composition as in claim 1, wherein the photosensitive substance is obtained by reacting a polyhydroxy compound having both at least one group represented by formula (II) and at least one group represented by formula (III) in the same molecule and a 1,2-naphthoquinonediazido-5-(and/or -4-)sulfonyl chloride in a mixed solvent comprising an organic solvent and water:

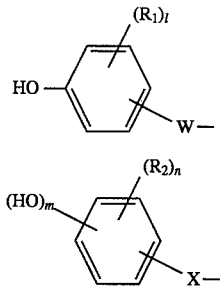

wherein W represents a linear or branched $C_1$ to $C_6$ alkylene group; X represents a divalent electron attracting group, or

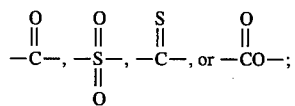

$R_1$ represents —H, a $C_1$ to $C_4$ alkyl group; $R_2$ represents —H, a $C_1$ to $C_4$ alkyl group, a halogen, a nitro group or a cyano group; l represents 0 or an integer of from 1 to 3; m represents an integer of from 1 to 4; and n represents 0 or an integer of from 1 to 4.

8. A positive photoresist composition as in claim 1, wherein the photosensitive substance is obtained by reacting a polyhydroxy compound having at least one group represented by formula (IV), (V) or (VI) per molecule and a 1,2-naphthoquinonediazido-5-(and/or -4-)-sulfonyl chloride in a mixed solvent comprising an organic solvent and water:

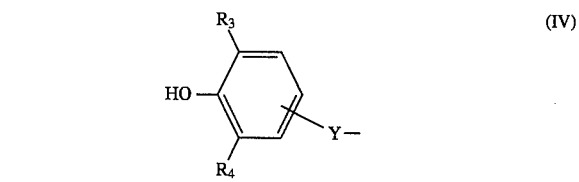

where $R_3$ and $R_4$ each represents —H, a linear or branched $C_1$ to $C_4$ alkyl or alkoxy group, provided that $R_3$ and $R_4$ are not both —H; and Y represents a divalent organic group which is a linear or branched $C_1$ to $C_4$ alkylene group,

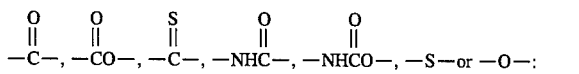

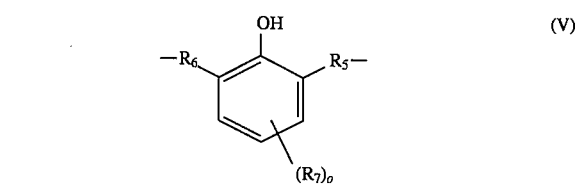

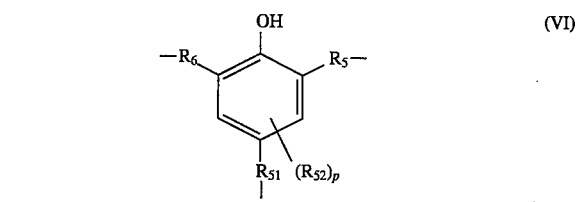

wherein $R_5$, $R_6$ and $R_{51}$ each represents a linear or branched $C_1$ to $C_4$ alkyl group; $R_7$ and $R_{52}$ may be the same or different and each represents —H, an alkyl group, an alkoxy group, an aryl group, an aralkyl group, an acyl group, or an acyloxy group; o represents 0 or an integer of from 1 to 3; and p represents 1 or 2.

9. A positive photoresist composition as in claim 7, wherein the photosensitive substance comprises a mixture of compounds obtained by reacting a polyhydroxy compound represented by one of formulae (VII') and (VIII'), respectively, and a 1,2-naphthoquinonediazido-5-(and/or -4-) sulfonyl chloride in a mixed solvent comprising an organic solvent and water:

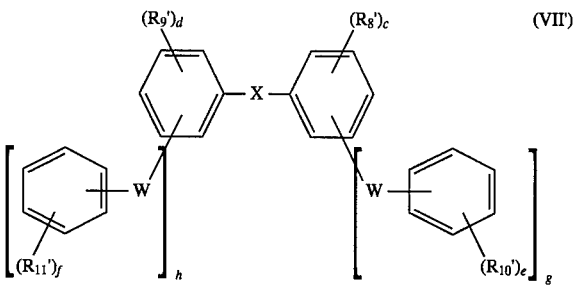

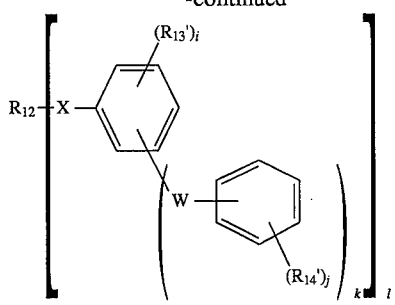

(VIII')

wherein W represents a linear or branched $C_1$ to $C_6$ alkylene group; X represents a divalent electron attracting group, or

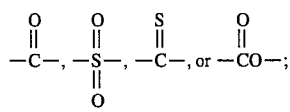

$R_{12}$ represents a $C_1$ to $C_4$ alkane residue, or a $C_6$ to $C_{12}$ aromatic residue; $R'_8$ to $R'_{11}$ and $R'_{13}$ and $R'_{14}$ may be the same or different and each represents —H, —OH, an unsubstituted alkyl group, an unsubstituted alkoxy group, an unsubstituted aryl group, an unsubstituted aralkyl group, an unsubstituted aliphatic or aromatic acyl group, an unsubstituted aliphatic or aromatic acyloxy group, an alkyl or alkoxy group each substituted by an alkoxy group, an aryloxy group, an aryl group, a hydroxyl group, a carboxyl group, a sulfonic acid group, an amino group, a nitro group, a silyl group, a silylether group, a cyano group, an aldehyde group, a mercapto group or a halogen atom, or an aryl or aralkyl group each substituted by an alkoxy group, an aryloxy group, an aryl group, a hydroxyl group, a carboxyl group, an amino group, a nitro group, a silyl group, a silylether group, a cyano group, an aldehyde group, a mercapto group or a halogen atom; and c to l are average real numbers which satisfy the following conditions:

$$c\sim l:\quad 3 \leq (c+d) \leq 8$$
$$1 \leq (e+f) \leq 8$$
$$1 \leq (g+h) \leq 4$$
$$1 \leq i\sim l \leq 4$$

10. A positive photoresist composition as in claim 1, wherein the photosensitive substance comprises a mixture of compounds obtained by reacting a polyhydroxy compound represented by one of formulae (IX') to (XVIII'), respectively, and a 1,2-naphthoquinone-diazido-5-(and/or -4-)sulfonyl chloride in a mixed solvent comprising an organic solvent and water:

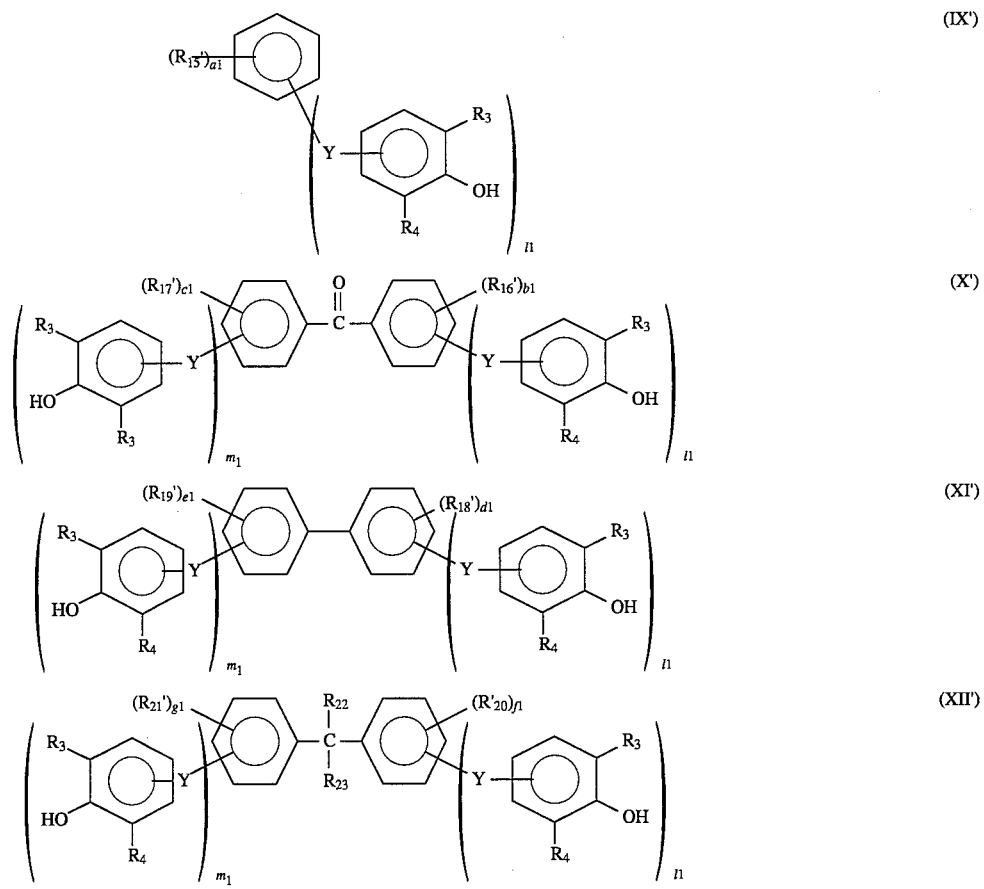

-continued
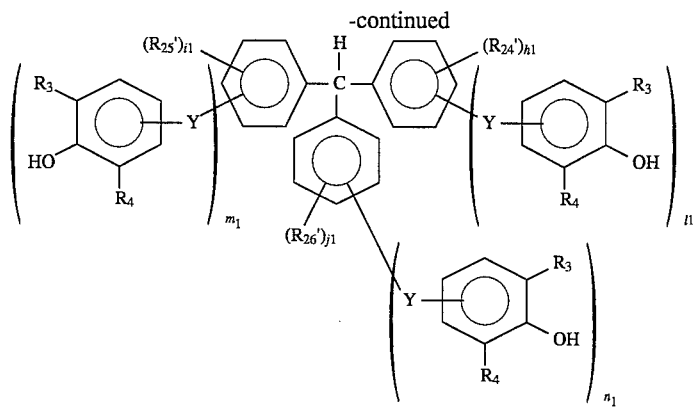
(XIII')
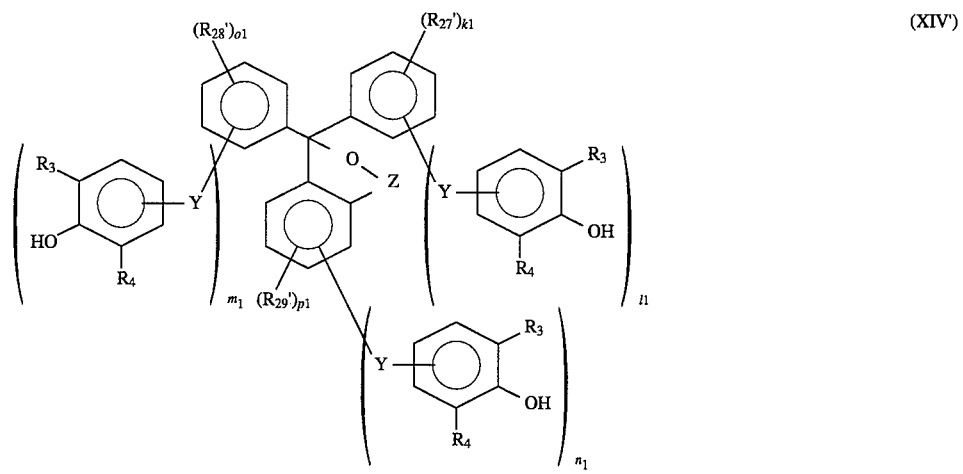
(XIV')
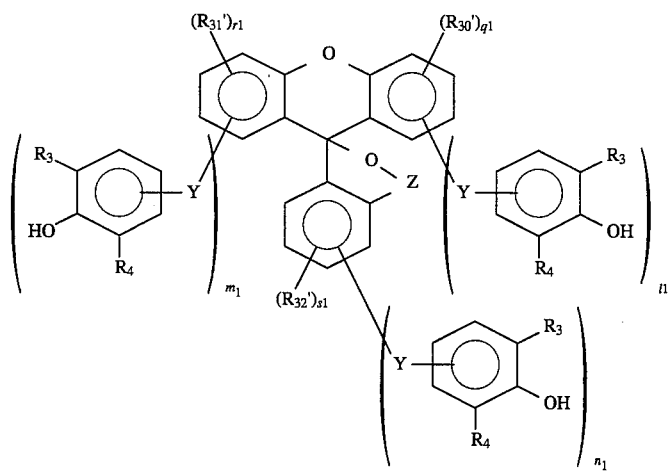
(XV')
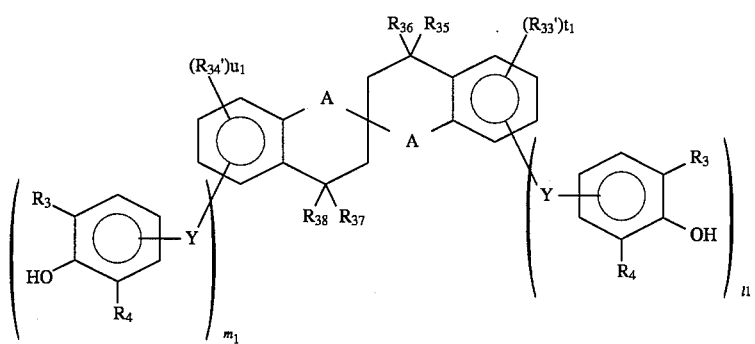
(XVI')

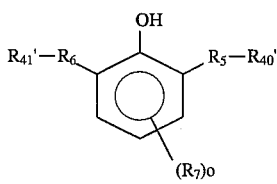

(XVII')

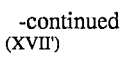

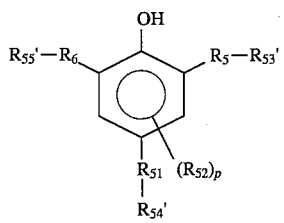

(XVIII')

wherein $R_3$ and $R_4$ each represent a linear or branched $C_1$ to $C_4$ alkyl or alkoxy group; Y represents a linear or branched $C_1$ to $C_4$ alkylene group, or

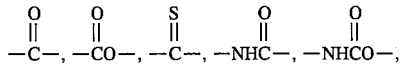

—S— or —O—; $R'_{15}$ to $R'_{21}$ and $R'_{24}$ to $R'_{34}$ may be the same or different and each represents —H, —OH, an unsubstituted alkyl group, an unsubstituted alkoxy group, an unsubstituted aryl group, an unsubstituted aralkyl group, an unsubstituted aliphatic or aromatic acyl group, an unsubstituted aliphatic or aromatic acyloxy, an alkyl or alkoxy group each substituted by an alkoxy group, an aryloxy group, an aryl group, a hydroxyl group, a carboxyl group, a sulfonic acid group, an amino group, a nitro group, a silyl group, a silylether group, a cyano group, an aldehyde group, a mercapto group or a halogen atom, or an aryl or aralkyl group each substituted by an alkoxy group, an aryloxy group, an aryl group, a hydroxyl group, a carboxyl group, an amino group, a nitro group, a silyl group, a silylether group, a cyano group, an aldehyde group, a mercapto group or a halogen atom; $R_{22}$ and $R_{23}$ each represents —H, —OH, —COOH, —CN, a halogen atom, —COOR$_{43}$, —R$_{44}$—COOH, —R$_{45}$—COOR$_{46}$ (where $R_{43}$ and $R_{46}$ each represent an alkyl group, an aryl group, an aralkyl group; and $R_{44}$ and $R_{45}$ each represents an alkylene group, or an arylene group), an unsubstituted alkyl group, an unsubstituted alkoxy group, an unsubstituted aryl group, an unsubstituted aralkyl group, an alkyl or alkoxy group each substituted by an alkoxy group, an aryloxy group, an aryl group, a hydroxyl group, a carboxyl group, a sulfonic acid group, an amino group, a nitro group, a silyl group, a silylether group, a cyano group, an aldehyde group, a mercapto group or a halogen atom, or an aryl or aralkyl group each substituted by an alkoxy group, an aryloxy group, an aryl group, a hydroxyl group, a carboxyl group, an amino group, a nitro group, a silyl group, a silylether group, a cyano group, an aldehyde group, a mercapto group or a halogen atom; Z represents —CO— or —SO$_2$—; A represents an oxygen atom or a single bond; a1 to u1 are average real numbers which satisfy the following conditions:

$$a1\text{~}u1: \quad 1 \leq a1 \leq 3$$
$$1 \leq l1 \leq 2$$
$$0 \leq m1, n1 \leq 2$$

$$3 \leq \begin{pmatrix} (b1+c1) \\ (d1+e1) \\ (f1+g1) \\ (t1+u1) \end{pmatrix} \leq 7$$

$$3 \leq \begin{pmatrix} (h1+i1+j1) \\ (k1+o1+p1) \\ (q1+r1+s1) \end{pmatrix} \leq 10$$

$R_5$, $R_6$ and $R_{51}$ each represents a linear or branched $C_1$ to $C_4$ alkylene group; $R_{35}$ to $R_{38}$ may be the same or different and each represents —H, —OH, an alkyl group, an alkoxy group, or an aralkyl group; $R'_{40}$, $R'_{41}$ and $R'_{54}$ each represents a residue of any of formulae (IX') to (XVI') where l1=m1=n=0, or a residue of an aldehyde condensate represented by the formula:

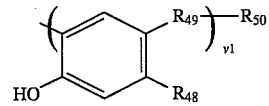

wherein $R_{48}$ represents an alkyl group, or an alkoxy group; $R_{49}$ represents an aldehyde residue; $R_{50}$ represents —H, or an aromatic residue; and v1 represents an integer of from 1 to 5.

* * * * *